United States Patent [19]

Kotewicz et al.

[11] Patent Number: 6,063,608
[45] Date of Patent: *May 16, 2000

[54] CLONED GENES ENCODING REVERSE TRANSCRIPTASE LACKING RNASE H ACTIVITY

[75] Inventors: Michael Leslie Kotewicz, Columbia; Gary Floyd Gerard, Frederick, both of Md.

[73] Assignee: Life Technologies, Inc., Rockville, Md.

[ * ] Notice: This patent is subject to a terminal disclaimer.

[21] Appl. No.: 08/798,458

[22] Filed: Feb. 10, 1997

Related U.S. Application Data

[63] Continuation of application No. 08/614,260, Mar. 12, 1996, Pat. No. 5,668,005, which is a continuation of application No. 08/404,907, Mar. 15, 1995, abandoned, which is a continuation of application No. 07/825,260, Jan. 24, 1992, Pat. No. 5,405,776, which is a division of application No. 07/671,156, Mar. 18, 1991, Pat. No. 5,244,797, which is a continuation of application No. 07/143,396, Jan. 13, 1988, abandoned.

[51] Int. Cl.[7] .............. C12N 9/12; C12N 15/54; C12N 15/70; C12P 19/34
[52] U.S. Cl. .......... 435/194; 435/69.1; 435/91.1; 435/91.2; 435/252.3; 435/252.33; 435/320.1; 435/475; 435/975; 536/23.2
[58] Field of Search .................. 435/194, 69.1, 435/252.3, 252.33, 320.1, 475, 91.1, 975, 69.4; 536/23.2

[56] References Cited

U.S. PATENT DOCUMENTS

| | | | |
|---|---|---|---|
| 4,663,290 | 5/1987 | Weis et al. | 435/253.33 |
| 4,795,699 | 1/1989 | Tabor et al. | 435/5 |
| 4,943,531 | 7/1990 | Goff et al. | 435/194 |
| 5,017,488 | 5/1991 | McAllister | 435/194 |
| 5,017,492 | 5/1991 | Kotewicz et al. | 435/252.3 |
| 5,244,797 | 9/1993 | Kotewicz et al. | 435/194 |
| 5,405,776 | 4/1995 | Kotewicz et al. | 435/194 |
| 5,668,005 | 9/1997 | Kotewicz et al. | 435/194 |

FOREIGN PATENT DOCUMENTS

WO 86/06741  11/1986  WIPO.

OTHER PUBLICATIONS

Goff, S. P., and Lobel, L.I., Biochimica et Biophysica Acta, vol. 907, "Mutants of murine leukemia viruses and retroviral replication", pp. 93–123, 1987.

DeStefano, J.J., et al., The Journal of Biological Chemistry, vol. 266, "Polymerization and RNase H activities of the reverse transcriptase from avian myeloblastosis, human immunodeficiency, and Moloney murine leukema viruses . . . ", pp. 7423–7431, 1991.

Buiser, R.G., et al., The Journal of Biological Chemistry, vol. 266, "Requirements for the catalysis of strand transfer synthesis by retroviral DNA polymerases", pp. 13103–13109, 1991.

Bryant, D. L., et al., Molecular and Cellular Biology, vol. 4, "Amino acid alterations within a highly conserved region of the Rous sarcoma virus src gene product pp60src inactivate tyrosine protein kinase activity", pp. 862–866, 1984.

(List continued on next page.)

Primary Examiner—Ponnathapu Achutamurthy
Assistant Examiner—William W. Moore
Attorney, Agent, or Firm—Sterne, Kessler, Goldstein, and Fox P.L.L.C.

[57] ABSTRACT

The invention relates to a gene which encodes reverse transcriptase having DNA polymerase activity and substantially no RNase H activity. The invention also relates to vectors containing the gene and hosts transformed with the vectors of the invention. The invention also relates to a method of producing reverse transcriptase having DNA polymerase activity and substantially no RNase H activity by expressing the reverse transcriptase genes of the present invention in a host. The invention also relates to a method of producing cDNA from mRNA using the reverse transcriptase of the invention. The invention also relates to a kit for the preparation of cDNA from mRNA comprising the reverse transcriptase of the invention.

196 Claims, 8 Drawing Sheets

OTHER PUBLICATIONS

Amuro, N., et al., The Journal of Biological Chemistry, vol. 260, "Replacement by site–directed mutagenesis indicates a role for histidine 170 in the glutamine amide transfer function of anthranilate synthase", pp. 14844–14849, 1985.

Ivanoff, L. A., et al., Proceedings of the National Academy of Scienes, U.S.A., vol. 83, "Expression and site–specific mutagenesis of the poliovirus 3C protease in Escherichia coli", pp. 5392–5396, 1986.

Voordouw, G., et al., European Journal of Biochemistry, vol. 163, "Side–directed mutagenesis of the small subunit of ribulose–1,5–bisphosphate carboxylase/oxygenase from Anacystis nidulans", pp. 591–598, 1987.

Houdebine, L–M., Nucleic Acids Research, vol. 3, "Synthesis of DNA complementary to the mRNAs for milk proteins by E. coli DNA polymerase I", pp. 615–630, 1976.

Joyce, C. M., et al., Proceedings of the National Academy of Sciences, U.S.A., vol. 80, "Construction of a plasmid that overproduces the large proteolytic fragment (Klenow fragment) of DNA polymerase I of Escherichia coli", pp. 1830–1834, 1983.

Gerard, G. F., et al., Focus, vol. 11, "cDNA synthesis by cloned Moloney murine leukemia virus reverse transcriptase lacking RNase H activity", pp. 66–69, published by Life Technologies, Inc., Gaithersburg, MD, 1989.

Akins, R.A. et al., "Mitochondrial Plasmids of Neurospora: Integration into Mitochondrial DNA and Evidence for Reverse Transcription in Mitochondria," *Cell* 47:505–516 (1986).

Bassin, R.H. et al., "Macromolecular Requirements for Abrogation of Fv–1 Restriction by Murine Leukemia Viruses," *J. Virology* 35(2):287–297 (1980).

Berger, S.L. et al., "Reverse Transcriptase and Its Associated Ribonuclease H: Interplay of Two Enzyme Activities Controls the Yield of Single–Stranded Complementary Deoxyribonucleic Acid," *Biochemistry* 23:2365–2372 (1983).

Blain, S.W. and Goff, S.P., "Nuclease Activities of Moloney Murine Leukemia Virus Reverse Transcriptase," *J. Biol. Chem.* 268(31):23585–23592 (1993).

Carter, P. and Wells, J.A., "Engineering Enzyme Specificity by 'Substrate–Assisted Catalysis,'" *Science* 237:394–399 (1987).

Fawcett, D.H. et al., "Transposable Elements Controlling I–R Hybrid Dysgenesis in *D. melanogaster* Are Similar to Mammalian Lines," *Cell* 47:1007–1015 (1986).

Finston, W.I. and Champoux, J.J., "RNA–Primed Intiation of Molony Murine Leukemia Virus Plus Strands by Reverse Transcriptase In Vitro," *J. Virology* 51(1):26–33 (1984).

Gerard, G.F. et al., "Poly (2'–O–methylcytidylate) Oligodeoxyguanylate as a Template for the Ribonucleic Acid Directed Deoxyribonucleic Acid Polymerase in Ribonucleic Acid Tumor Virus Particles and a Specific Probe for the Ribonucleic Acid Directed Enzyme in Transformed Murine Cells," *Biochemistry* 13(8):1632–1641 (1974).

Gerard, G.F. and Grandgenett, D.P., "Purification and Characterization of the DNA Polymerase and RNase H Activities in Moloney Murine Sarcoma–Leukemia Virus," *J. Virology* 15(4):785–797 (1975).

Gerard, G.F., "Multiple RNase H Activities in Mammalian Type C Retravirus Lysates," *J. Virology* 26(1):16–28 (1978).

Gerard, G.F., "Mechanism of Action of Moloney Murine Leukemia Virus RNase H III," *J. Virology* 37(2):748–754 (1981).

Gerard, G.F. et al., "Influence on Stability in *Escherichia coli* of the Carboxy–Terminal Structure of Cloned Moloney Murine Leukemia Virus Reverse Transcriptase," *DNA* 5(4):271–279 (1986).

Gerwin, B.I. et al., "Mutant of B–Tropic Murine Leukemia Virus Synthesizing an Altered Polymerase Molecule," *J. Virology* 31(3):741–751 (1979).

Gorecki, M. and Panet, A., "Discrimination of DNA Polymerase and RNase H Activities in Reverse Transcriptase of Avian Myeloblastosis Virus," *Biochemistry* 17(12):2438–2442 (1978).

Johnson, M.S. et al., "Computer analysis of retroviral pol genes: Assignment of enzymatic functions to specific sequences and homologies with nonviral enzymes," *Proc. Natl. Acad. Sci. USA* 83(20):7648–7652 (1986).

Kamer, G. and Argos, P., "Primary structural comparison of RNA–dependent polymerases from plant, animal and bacterial viruses," *Nucl. Acids. Res.* 12(18):7629–7282 (1984).

Kotewicz, M.L. et al., "Cloning and overexpression of Moloney murine leukemia virus reverse transcriptase in *Escherichia coli,*" *Gene* 35:249–258 (1985).

Kotewicz, M.L. et al., "Isolation of cloned Moloney murine leukemia virus reverse transcriptase lacking ribonuclease H activity," *Nucl. Acids Res.* 16(1):265–277 (1988).

Lai, M.–H.T. and Verma, I.M., "Reverse Transcriptase of RNA Tumor Viruses. V. In Vitro Proteolysis of Reverse Transcriptase from Avian Myeloblastosis Virus and Isolation of a Polypeptide Manifesting Only RNase H Activity," *J. Virology* 25(2):652–663 (1978).

Lai, M.–H.T. et al., "Mammalian Retrovirus–Associated RNase H Is Virus Coded," *J. Virology* 27(3):823–825 (1978).

Levin, J.G. et al., "Murine Leukemia Virus Mutant with a Frameshift in the Reverse Transcriptase Coding Region: Implications for pol Gene Structure," *J. Virology* 51(2):470–478 (1984).

Maniatis, T. In: *Molecular Cloning. A Laboratory Manual*, Cold Spring Harbor Laboratory Press, pp. 213 and 231 (1982).

Meloun, B. et al., "Complete primary structure of thermitase from *Thermoactinomyces vulgaris* and its structural features related to the subtilisin–type proteinases," *FEBS Letters* 183(2):195–200 (1985).

Messer, L.I. et al., "Functional Analysis of Reverse Transcription by a Frameshift pol Mutant of Murine Leukemia Virus," *Virology* 146:146–152 (1985).

Michel, F. and Lang, B.F., "Mitochondrial class II introns encode proteins related to the reverse transcriptases of retroviruses," *Nature* 316:641–643 (1985).

Moelling, K. and Friis, R.R., "Two Avian Sarcoma Virus Mutants with Defects in the DNA Polymerase–RNase H Complex," *J. Virology* 32(2):370–378 (1979).

Resnick, R. et al., "Involvement of Retrovirus Reverse Transcriptase–Associated RNase H in the Initiation of Strong–Stop (+) DNA Synthesis and the Generation of the Long Terminal Repeat," *J. Virology* 51(3):831–821 (1984).

Roth, M.J. et al., "Purification and Characterization of Murine Retroviral Reverse Transcriptase Expressed in *Escherichia coli,*" *J. Biol. Chem.* 260(16):9326–9335 (1985).

Shinnick, T.M. et al., "Nucleotide sequence of Moloney murine leukaemia virus," *Nature* 293:543–548 (1981).

Smith, J.K. et al., "Initiation of Plus–Strand DNA Synthesis During Reverse Transcription of an Avian Retrovirus Genome," *J. Virology* 49(1):200–204 (1984).

Tanese, N. et al., "Analysis of Retroviral pol Gene Products with Antisera Raised against Fusion Proteins Produced in *Escherichia coli,*" *J. Virology* 59(2):328–340 (1986).

Tanese, N. et al., "Expression of enzymatically active reverse transcriptase in *Escherichia coli,*" *Proc. Natl. Acad. Sci. USA* 82(15):4944–4948 (1985).

Telesnitsky, A. and Goff, S.P., "RNase H domain mutations affect the interaction between Moloney murine leukemia virus reverse transcriptase and its primer–template," *Proc. Natl. Acad. Sci. USA* 90:1276–1280 (1993).

Toh, H. et al., "Sequence homology between retroviral reverse transcriptase and putative polymerases of hepatitis B virus and cauliflower mosaic virus," *Nature* 305:827–829 (1983).

Tronick, S.R. et al., "Molecular cloning of Moloney murine sarcoma virus: Arrangement of virus–related sequences within the normal mouse genome," *Proc. Natl. Acad. Sci. USA* 76(12):6314–6318 (1979).

Van Beveren, C. et al., "RNA Tumor Viruses" in *Molecular Biology of Tumor Viruses*, 2nd ed., vol. 2. Cold Spring Harbor Laboratory Press, pp. 773–779 (1985).

Zoller, M.J. and Smith, M., "Oligonucleotide–Directed Mutagenesis of DNA Fragments Cloned into M13 Vectors," *Methods in Enzymology* 100:468–500 (1983).

Brewer, L.C. and Wells, R.D., "Mechanistic Independence of Avian Myeloblastosis Virus DNA Polymerase and Ribonucleases H," *J. Virol.* 14:1494–1502 (1974).

Kimmel, A.R. and Berger, S.L., "Preparation of cDNA and the Generation of cDNA Libraries: Overview," *Meth. Enzymol.* 152:307–389 (1987).

Myers, J.C. and Spiegelman, S., "Sodium pyrophosphate inhibition of RNA•DNA hybrid degradation by reverse tanscriptase," *PNAS USA*:75:5329–5333 (1978).

Rho, H.M., "Biochemical and Immunological Characterization of the DNA Polymerase and RNase H in Feline Leukemia Virus," *Korean J. Zoology* 22:141–152 (1979).

Rho, H.M. and Gallo, R.C., "Biochemical and Immunological Properties of the DNA Polymerase and RNAase H Activities of Purified Feline Leukemia Virus Reverse Transcriptase," *Cancer Letters* 10:207–221 (1980).

Weiss, J. et al., "Production and Characterization or Monoclonal Antibodies Against Avian Retrovirus Reverse Transcriptase," *J. Virol.* 45:859–863 (1983).

Weiss, R. et al., eds., *Molecular Biology of Tumor Viruses*, 2d edition, Chapter 5, "RNA Tumor Viruses," pp. 75–80, Cold Spring Harbor Laboratory (1985).

Berger, S.L. et al., "Reverse Transcriptase and Its Associated Ribonuclease H: Interplay of Two Enzyme Activities Controls the Yield of Single–Stranded Complementary Deoxyribonucleic Acid," *Biochem.* 22:2365–2372 (1983).

Dudding, L.R. et al., "Analysis of the RNA– and DNA–Dependent DNA Polymerase Activities of Point Mutants of HIV–1 Reverse Transcriptase Lacking Ribonuclease H Activity," *Biochem.* 30:10498–10506 (Oct. 1991).

Gubler, U. and Hoffman, B.J., "A simple and very efficient method for generating cDNA libraries," *Gene* 25:263–269 (Nov. 1983).

Hizi, A. et al., "Mutational Analysis of the Ribonuclease H Activity of Human Immunodeficiency Virus 1 Reverse Transcriptase," *Virol.* 175:575–580 (Apr. 1990).

Houts, G.E. et al., "Reverse Transcriptase from Avian Myeloblastosis Virus," *J. Virol.* 29:517–522 (Feb. 1979).

Kanaya, S. et al., "Identification of the Amino Residues Involved in an Active Site of *Escherichia coli* Ribonuclease H by Site–directed Mutagenesis," *J. Biol. Chem.* 265:4615–4621 (Mar. 1990).

Mizrahi, V. et al., "Site–directed mutagenesis of the conserved Asp–443 and Asp–498 carboxy–terminal residues of HIV–1 reverse transcriptase," *Nucl. Acids Res.* 18:5359–5363 (Sep. 1990).

Repaske, R. et al., "Inhibition of RNase H Activity and Viral Replication by Single Mutations in the 3' Region of Moloney Murine Leukemia Virus Reverse Transcriptase," *J. Virol.* 63:1460–1464 (Mar. 1989).

Schwartzberg, P. et al., "Construction and Analysis of Deletion Mutations in the pol Gene of Moloney Murine Leukemia Virus: A New Viral Function Required for Productive Infection," *Cell* 37:1043–1052 (Jul. 1984).

Tanese, N. and Goff, S.P., "Fine–Structure Mutational Analysis of the Reverse Transcriptase Domain of Moloney Murine Leukemia Virus," *RNA Tumor Viruses*, Cold Spring Harbor Laboratory, Cold Spring Harbor, New York (May 19–May 24, 1987).

Telesnitsky, A. and Goff, S.P., "RNase H domain mutations affect the interaction between Moloney murine leukemia virus reverse transcriptase and its primer–template," *Proc. Natl. Acad. Sci. USA* 90:1276–1280 (Feb. 1993).

"Defendant's Supplemental Response to Plaintiff's Interrogatory No. 13," dated May 15, 1998 from *Life Technologies, Inc. v. Clontech Laboratories, Inc.*, U.S. District Court for the District of Maryland, Civil Action No. AW 96–4080.

Letter dated Oct. 9, 1987 from John E. Donelson, Exec. Editor of Nucleic Acids Research, Exhibit LTX 6402 from *Life Technologies, Inc. v. Clontech Laboratories, Inc.*, U.S. District Court for the District of Maryland, Civil Action No. AW 96–4080.

Referee's Report on Kotewicz' et al., "Isolation of cloned Moloney murine leukemia virus . . . ," Exhibit LTX 6403 from *Life Technologies, Inc. v. Clontech Laboratories, Inc.*, U.S. District Court for the District of Maryland, Civil Action No. AW 96–4080 (Oct. 1987).

Referee's Report on Kotewicz' et al., "Isolation of cloned Moloney murine leukemia virus . . . ," Exhibit LTX 6404 from *Life Technologies, Inc. v. Clontech Laboratories, Inc.*, U.S. District Court for the District of Maryland, Civil Action No. AW 96–4080 (Oct., 1987).

Letter dated Nov. 17, 1987, from Gary F. Gerard, Ph.D., Director Enzymology, Nucleic Acids & Recombinant DNA, Molecular Biology R&D, of Bethesda Research Laboratories, Life Technologies, Inc., Exhibitis LTX 6405 and LTX 6406 in *Life Technologies, Inc. v. Clontech Laboratories, Inc.*, U.S. District Court for the District of Maryland, Civil Action No. AW 96–4080.

"Approval of Scientific Publications" form, Michael L. Kotewicz, requestor, dated Jul. 24, 1987, with note attached, Exhibits LTX 6407 and LTX 6408 from *Life Technologies, Inc. v. Clontech Laboratories, Inc.*, U.S. Distrct Court for the District of Maryland, Civil Action No. AW 96–4080.

Memorandum from Dietmar Rabussay dated Aug. 18, 1987, Exhibits LTX 6409 and LTX 6410 from *Life Technologies, Inc. v. Clontech Laboratories, Inc.*, U.S. District Court for the District of Maryland, Civil Action No. AW 96–4080.

Defendant's "Answer" dated Jan. 24, 1995 from *Life Technologies, Inc. v. Promega Corporation*, U.S. District Court for the District of Maryland, Civil Action No. AW 94–2776.

"Consent Judgment" dated Mar. 31, 1995 from *Life Technologies, Inc. v. Promega Corporation*, U.S. District Court for the District of Maryland, Civil Action No. AW 94–2776.

Defendant's "Answer and Couterclaim" dated Feb. 6, 1995 from *Life Technologies, Inc. v. Stratagene, Inc.*, U.S. District Court for the District of Maryland, Civil Action No. AW 94–2777.

"Memorandum Opinion" dated Jul. 27, 1995 from *Life Technologies, Inc. v. Stratagene, Inc.*, U.S. District Court for the District of Maryland, Civil Action No. AW 94–2777.

"Order" dated Jul. 27, 1995 from *Life Technologies, Inc. v. Stratagene, Inc.*, U.S. District Court for the District of Maryland, Civil Action No. AW 94–2777.

"Stratagene's Responses and Objections to Plaintiff's Second Set of Interrogatories to Defendant and Second Request for Production of Documents and Things" dated Aug. 7, 1995, from *Life Technologies, Inc. v. Stratagene, Inc.*, U.S. District Court for the District of Maryland, Civil Action No. AW 94–2777, including (a) Weis, *J. Virol.* 45:859–863 (1983); (b) Rho & Gallo, *Cancer Letters* 10:207–221 (1980) and (c) Rho, *Korean Journal of Zoology* 22:141–152 (1970).

Defendant's "Amended Answer and Affirmative Defenses" dated Jul. 11, 1997 from *Life Technologies, Inc. v. Clontech Laboratories, Inc.*, U.S. District Court for the District of Maryland, Civil Action No. AW–96–4080.

"Life Technologies, Inc., Invention Disclosure Form" dated Apr. 30, 1987, Exhibit Nos. LTX32497–LTX32502, from *Life Technologies, Inc. v. Clontech Laboratories, Inc.*, U.S. District Court for the District of Maryland, Civil Action No. AW–96–4080.

Handwritten note by Brian Schmidt, employee of Life Technologies, Inc., Exhibit LTX35171 in *Life Technologies, Inc. v. Clontech Laboratories, Inc.*, U.S. District Court for the District of Maryland, Civil Action No. AW 96–4080 [1990].

"Complaint" dated Dec. 22, 1998, from *Clontech Laboratories, Inc. v. Life Technologies, Inc.*, U.S. District Court for the District of Delaware, Civil Action No. 98–750.

"Memorandum Opinion" and accompanying "Order" dated Feb. 18, 1999, from *Life Technologies, Inc. v. Clontech Laboratories, Inc.*, U.S. District Court for the District of Maryland, Southern Division, Civil Action No. AW–96–4080.

Copeland, T.D. et al., "Amino– and Carboxyl–Terminal Sequence of Moloney Murine Leukemia Virus Reverse Transcriptase," *Virology* 143:676–679 (1985).

Crouch,R. and Dirksen, M.–L., "Ribonucleases H", in *Nucleases*, Linn, S. and Roberts, R., eds., Cold Spring Harbor Laboratory Press, Cold Spring Harbor, N.Y., pp. 211–241 (1982).

Freeman–Wittig, M.–J. et al., "Differential Effects of Captan on DNA Polymerase and Ribonuclease H Activities of Avian Myeloblastosis Virus Reverse Transcriptase," *Biochemistry* 25:3050–3055 (1986).

Freeman–Wittig, M.–J. et al., "Captan binding to avian myeloblastosis virus reverse transcriptase and its effect on RNase H activity," *Mol. Cell. Biochem.* 94:9–17 (1990).

Gerard, G., "Comparison of cDNA Synthesis by Avian and Cloned Murine Reverse Transcriptase," *Focus* 7:1–3 (1985).

Gerard, G. et al., "cDNA Synthesis by Moloney Murine Leukemia Virus RNase H–Minus Reverse Transcriptase Possessing Full DNA Polymerase Activity," *Focus* 14:91–93 (1994).

Goff, S.P., "Genetic and Biochemical Approach to the Study of Retroviral Replication", Abstract from the 7th Annual DNA Congress, San Francisco, CA (Mar. 1987).

Grandgenett, D. et al., "Activiation of an $MG^{2+}$–Dependent DNA Endonuclease of Avian Myeloblastosis Virus αβ DNA Polymerase by In Vitro Proteolytic Cleavage," *J. Virology* 33:264–271 (1980).

Grandgenett, D. et al., "Structural Characterization of the Avian Retrovirus Reverse Transcriptase and Endonulcease Domains," *J. Biol. Chem.* 260:8243–8249 (1985).

Green, M. and Gerard, G., "RNA–Directed DNA Polymerase–Properties and Functions in Oncogenic RNA Viruses and Cells," *Progress in Nucleic Acid Research and Molecular Biology* 14:188–334 (1974).

Hansen, J. et al., "Identification and characterization of HIV–specific RNase H by monoclonal antibody," *EMBO J.* 7:239–243 (1988).

Hizi, A. et al., "Expression of soluble, enzymatically active, human immunodeficiency virus reverse transcriptase in *Escherichia coli* and analysis of mutants," *Proc. Natl. Acad. Sci. USA* 85:1218–1222 (1988).

Hizi, A. et al., "The Effects of Cysteine Mutations on Reverse Transcriptase of Human Immunodeficiency Virus Types 1 and 2," *J. Biol. Chem.* 267:1293–1297 (1992).

Holmes, M. H., "Elimination of Unwanted Restriction Sites from a Plasmid Bearing the Reverse Transcriptase Gene of Moloney Murine Leukemia Virus," University of Maryland, Baltimore County, MD, Oct. 6, 1986.

Hostomsky, S. et al., "Ribonucleases H," in *Nucleases, 2nd ed.*, Linn, S. and Roberts, R., eds. Cold Spring Harbor Laboratory Press, Cold Spring Harbor, NY, pp. 341–376 (1993).

Jacobsen, H. et al., "The N–Terminal Amino–Acid Sequences of DNA Polymerase I from *Escherichia coli* and of the Large and the Small Fragments Obtained by a Limited Proteolysis," *Eur. J. Biochem.* 45:623–627 (1974).

Katayanagi, K. et al., "Crystal Structures of Ribonuclease HI Active Site Mutants from *Escherichia coli,*" *J. Biol. Chem.* 268:22092–22099 (1993).

Klenow, H. and Henningsen, "Selective Elimination of the Exonuclease Activity of the Deoxyribonucleic Acid Polymerase from *Escherichia coli* B by Limited Proteolysis," *Proc. Natl. Acad. Sci. USA,* 65:168–175 (1970).

Gerard, G., Inhibition of Superscript II Reverse Transcriptase by Common Laboratory Chemicals, Documents regarding CAT Transcription Detection and SuperScript RNase H⁻ Reverse Transcriptase brochure, from *Life Technologies, Inc. v. Clonetech Laboratories, Inc.*, U.S. District Court for the District of Maryland Southern Division, Civil Action No. AW96–4080, LTX18287–LTX18318, and LTX18321–LTX18344. [1999].

Margalith, M. et al., "Differential inhibition of DNA polymerase and RNase H activities of the reverse transcriptase by phosphonoformate," *Mol. Cell. Biochem.* 43:97–103 (1982).

Mizrahi, V. et al., "Recombinant HIV–1 Reverse Transcriptase: Purification, Primary Structure, and Polymerase/Ribonuclease H Activities," *Arch. Biochem. Biophys.* 273:347–358 (1989).

Modak, M.J. and Marcus, S.L., "Purification and Properties of Rauscher Leukemia Virus DNA Polymerase and Selective Inhibition of Mammalian Viral Reverse Transcriptase by Inorganic Phosphate," *J. Biol. Chem.* 252:11–19 (1977).

Nakamura, H. et al., "Structural models of ribonuclease H domains in reverse transcriptase from retroviruses," *Nucleic Acids Res. 19*:1817–1823 (1991).

Prasad, V. and Goff, S., "Linker insertion mutagenesis of the human immunodeficiency virus reverse transcriptase expressed in bacteria: Definition of the minimal polymerase domain," *Proc. Natl. Acad. Sci. USA 86*:3104–3108 (1989).

Roth, M. et al., "Purification and Characterization of Murine Retroviral reverse Transcriptase Expressed in *Escherichia coli*," *J. Biol. Chem. 260*:9326–9335 (1985).

Schatz, O. et al., "Point mutations in conserved amino acid residues within the C–terminal domain of HIV–1 reverse transcriptase specifically repress RNase H function," *FEBS Lett. 257*:311–314 (1989).

Schatz, O. et al., "Inactivation of the RNase H Domain of HIV–1 Reverse Transcriptase Blocks Viral Infectivity," *Adv. Appl. Biotech. Series 7*:293–303 (1989).

Skalka and Goff, S. eds., *Reverse Transcriptase*, Cold Spring Harbor Laboratory Press, Cold Spring Harbor, N.Y. (1993).

Tanese, M. and Goff, S., "Domain Structure of the Moloney Murine Leukemia Virus Reverse Transcriptase: Mutational Analysis and Separate Expression of the DNA Polymerase and RNase H Activities," *Proc. Natl. Acad. Sci. USA 85*:1777–1781 (1988).

Telesnitsky, A. et al., "Defects in Moloney Murine Leukemia Virus Replication Caused by a Reverse Transcriptase Mutation Modeled on the Structure of *Escherichia coli* RNase H," *J. Virology 66*:615–622 (1992).

Tisdale, M. et al., "Mutations within the RNAse H domain of human immunodeficiency virus type 1 reverse transcriptase abolish virus infectivity," *J. General Virology 72*:59–66 (1991).

Varmus, H. and Swanstrom, R., "Replication of Retroviruses," in *Molecular Biology of Tumor Viruses, RNA Tumor Viruses* $2^{nd}$ ed., Cold Spring Harbor Laboratory Press, Cold Spring harbor, N.Y., pp. 369–512 (1982).

Zhan,X. et al., "The Isolated RNase H Domain of Murine Luekemia Virus Reverse Transcriptase," *J. Biol. Chem. 272*:22023–22039 (1997).

"Defendant's Notice Pursuant to 35 U.S.C. §282," from *Life Technologies, Inc. v. Clonetech Laboratories, Inc.*, U.S. District Court for the District of Maryland Southern Division, Civil Action No. AW96–4080, pp. 1–8. [1999].

"Transcript of Motions Hearing Before the Honorable Alexander Williams, Jr., United States District Judge," dated Jul. 13, 1999, pp. 1–48 from *Life Technologies, Inc. v. Clontech Laboratories, Inc.*, U.S. District Court for the District of Maryland, Southern Division, Civil Action No. AW–96–4080.

"Transcript of Motions Hearing Before the Honorable Alexander Williams, Jr., United States District Judge" (Direct examination of Michael Leslie Kotewicz), dated Jul. 13, 1999, pp. 1–65, from *Life Technologies, Inc. v. Clontech Laboratories, Inc.*, U.S. District Court for the District of Maryland, Southern Division, Civil Action No. AW–96–4080.

"Morning Session" (Direct examination of Michael Leslie Kotewicz, cross examination of Michael Leslie Kotewicz, redirect examination of Michael Leslie Kotewicz, recross examination of Michael Leslie Kotewicz, direct examination of Robert Esmond), dated Jul. 14, 1999, pp. 66–163, from *Life Technologies, Inc. v. Clontech Laboratories, Inc.*, U.S. District Court for the District of Maryland, Southern Division, Civil Action No. AW–96–4080.

"Afternoon Session" (Direct examination of Robert Esmond, cross examination of Robert Esmond, direct examination of Harry F. Manbeck, cross examination of Harry F. Manbeck, redirect examination of Harry F. Manbeck, direct examination of Gary Floyd Gerard), dated Jul. 14, 1999, pp. 164–259, from *Life Technologies, Inc. v. Clontech Laboratories, Inc.*, U.S. District Court for the District of Maryland, Southern Division, Civil Action No. AW–96–4080.

"Morning Session" (Direct examination of Gary Floyd Gerard, cross examination of Gary Floyd Gerard, redirect examination of Gary Floyd Gerard, recross examination of Gary Floyd Gerard, direct examination of James J. Champoux, cross examination of James J. Champoux, redirect examination of James J. Champoux), dated Jul. 15, 1999, pp. 260–352, from *Life Technologies, Inc. v. Clontech Laboratories, Inc.*, U.S. District Court for the District of Maryland, Southern Division, Civil Action No. AW–96–4080.

"Transcript of Motions Hearing Before the Honorable Alexander Williams, Jr., United States District Judge" (Decision of the court), dated Jul. 16, 1999, pp. 423–451, from *Life Technologies, Inc. v. Clontech Laboratories, Inc.*, U.S. District Court for the District of Maryland, Southern Division, Civil Action No. AW–96–4080.

Garnier, J. et al., "Analysis of the Acuracy and Implications of Simple Methods for Predicting the Secondary Structure of Globular Proteins," *J. Mol. Biol. 120*:97–120 (1978).

Gerard, G.F., "Chapter 1. Reverse Transcriptase," in *Enzymes of Nucleic Acid Synthesis and Modification, vol. I, DNA Enzymes*, Jacob, S.T., ed., CRC Press, Inc., Boca Raton, FL, pp. 1–38 (1983).

Grandgenett, D.P et al., "A Single Subunit from Avian Myeloblastosis Virus with Both RNA–Directed DNA Polymerase and Ribonculease H Activity," *Proc. Natl. Acad. Sci. USA 70*:230–234 (1973).

Moelling, K., "Characterization of Reverse Transcriptase and RNase H from Friend–Murine Leukemia Virus," *Virology 62*:46–59 (1974).

Moelling, K., "Further Characterization of the Friend Murine Leukemia Virus Reverse Transcriptase–RNase H Complex," *J. Virol. 18*:418–425 (1976).

Old, R.W. and S.B. Primrose, "Cloning cDNA by Homopolymer Tailing," in *Principles of Gene Manipulation, An Introduction to Genetic Engineering*, 2nd Ed., University of California Press, Los Angeles, CA, pp. 26–27 (1981).

Omer, C.A. and A.J. Fares, "Mechanism of Release of the Avian Retroviruses tRNA$^{Trp}$ Primer Molecule from Viral DNA by Ribonuclease H During Reverse Transcription," *Cell 30*:797–805 (1982).

Toh, H. et al., "Close structural resemblance between putative polymerase of a *Drosphila* transposable genetic element 17.6 and pol gene product of Moloney murine leukaemia virus," *EMBO J. 4*:1267–1272 (1985).

Varmus, H., "Mechanisms Involved in the Synthesis of Retroviral DNA," in *RNA Tumor Viruses*, Weiss, R. et al., eds., Cold Spring Harbor Laboratory, pp. 410–423 (1982).

Defendant's Exhibit No. 14, LTX32496–LTX32502, from *Life Technologies, Inc. v. Clontech Laboratories, Inc.*, U.S. District Court for the District of Maryland, Southern Division, Civil Action No. AW–96–4080. [1999].

Defendant's Exhibit No. 50, LTX34776–LTX34780, from *Life Technologies, Inc. v. Clontech Laboratories, Inc.*, U.S. District Court for the District of Maryland, Southern Division, Civil Action No. AW–96–4080. [1999].

Defendant's Exhibit No. 88, LTX277–LTX281, from *Life Technologies, Inc. v. Clontech Laboratories, Inc.*, U.S. District Court for the District of Maryland, Southern Division, Civil Action No. AW–96–4080. [1999].

Defendant's Exhibit No. 124, LTX35319–LTX35320, from *Life Technologies, Inc. v. Clontech Laboratories, Inc.*, U.S. District Court for the District of Maryland, Southern Division, Civil Action No. AW–96–4080. [1999].

Defendant's Exhibit No. 136, LTX35341–LTX35343, from *Life Technologies, Inc. v. Clontech Laboratories, Inc.*, U.S. District Court for the District of Maryland, Southern Division, Civil Action No. AW–96–4080. [1999].

Defendant's Exhibit No. 137, LTX35344–LTX35345, from *Life Technologies, Inc. v. Clontech Laboratories, Inc.*, U.S. District Court for the District of Maryland, Southern Division, Civil Action No. AW–96–4080. [1999].

Defendant's Exhibit No. 138, LTX35346–LTX35348, from *Life Technologies, Inc. v. Clontech Laboratories, Inc.*, U.S. District Court for the District of Maryland, Southern Division, Civil Action No. AW–96–4080. [1999].

Defendant's Exhibit No. 237, LTX6408, from *Life Technologies, Inc. v. Clontech Laboratories, Inc.*, U.S. District Court for the District of Maryland, Southern Division, Civil Action No. AW–96–4080. [1999].

Defendant's Exhibit No. 238, LTX6409–LTX6410, from *Life Technologies, Inc. v. Clontech Laboratories, Inc.*, U.S. District Court for the District for Maryland, Southern Division, Civil Action No. AW–96–4080. [1999].

Defendant's Exhibit No. 259, LTX34739–LTX34763, from *Life Technologies, Inc. v. Clontech Laboratories, Inc.*, U.S. District Court for the District of Maryland, Southern Division, Civil Action No. AW–96–4080. [1999].

Defendant's Exhibit No. 394, from *Life Technologies, Inc. v. Clontech Laboratories, Inc.*, U.S. District Court for the District of Maryland, Southern Division, Civil Action No. AW–96–4080. [1999].

Defendant's Exhibit No. 399, from *Life Technologies, Inc. v. Clontech Laboratories, Inc.*, U.S. District Court for the District of Maryland, Southern Division, Civil Action No. AW–96–4080. [1999].

Defendant's Exhibit No. 398, from *Life Technologies, Inc. v. Clontech Laboratories, Inc.*, U.S. District Court for the District of Maryland, Southern Division, Civil Action No. AW–96–4080. [1999].

Defendant's Exhibit No. 397, from *Life Technologies, Inc. v. Clontech Laboratories, Inc.*, U.S. District Court for the District of Maryland, Southern Division, Civil Action No. AW–96–4080. [1999].

Defendant's Exhibit No. 396, from *Life Technologies, Inc. v. Clontech Laboratories, Inc.*, U.S. District Court for the District of Maryland, Southern Division, Civil Action No. AW–96–4080. [1999].

Defendant's Exhibit No. 401, from *Life Technologies, Inc. v. Clontech Laboratories, Inc.*, U.S. District Court for the District of Maryland, Southern Division, Civil Action No. AW–96–4080. [1999].

Defendant's Exhibit No. 433, from *Life Technologies, Inc. v. Clontech Laboratories, Inc.*, U.S. District Court for the District of Maryland, Southern Division, Civil Action No. AW–96–4080. [1999].

"Subpoena in a Civil Case" dated Aug. 21, 1997, served upon Stephen P. Goff, *Life Technologies, Inc. v. Clontech Laboratories, Inc.*, Civil Action No. AW 96–4080, U.S. District Court for the District of Maryland, Southern Division.

"Stipulation and Protective Order Re Confidential Documents of Non–Parties Columbia University and Dr. Stephen P. Goff," *Life Technologies, Inc. v. Clontech Laboratories, Inc.*, Civil Action No. AW 96–4080, U.S. District Court for the District of Maryland, Southern Division. [1999].

Letter from AYCC to Robert W. Esmond dated Dec. 10, 1999.

```
                                                              1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val

1258
TCC ATA AAA CAA TAC CCC ATG TCA CAA GAA GCC AGA CTG GGG ATC AAG CCC CAC ATA CAG
Ser Ile Lys Gln Tyr Pro MET Ser Gln Glu Ala Arg Leu Gly Ile Lys Pro His Ile Gln

1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu

1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg
```

FIG.6A

```
                                                                    1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile

1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe

1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu

1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly

1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala

1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp

1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln

1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu

2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp
```

FIG.6B

```
                                                                     2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT AAT TCC
Pro Ala Thr Leu Leu Pro Leu Pro Glu Glu Gly Leu Gln His Asn Cys Leu Asp Asn Ser

2533
CGC TTA ATT AAT TAA
Arg Leu Ile Asn
```

FIG. 6C

CLONED GENES ENCODING REVERSE TRANSCRIPTASE LACKING RNASE H ACTIVITY

This application is a continuation of application Ser. No. 08/614,260, filed Mar. 12, 1996 and issued as U.S. Pat. No. 5,668,005, continuation of application Ser. No. 08/404,907, filed Mar. 15, 1995 (abandoned), which is a continuation of application Ser. No. 07/825,260, filed Jan. 24, 1992 (granted, U.S. Pat. No. 5,405,776), which is a divisional of application Ser. No. 07/671,156, filed Mar. 18, 1991 (granted, U.S. Pat. No. 5,244,797), which is a continuation of application Ser. No. 07/143,393, filed Jan. 13, 1988 (abandoned).

FIELD OF THE INVENTION

The invention is in the field of recombinant genetics.

BACKGROUND OF THE INVENTION

Both viral and cloned reverse transcriptase (RT) contain at least two enzymatic activities, DNA polymerase and ribonuclease H (RNase H), that reside on a single polypeptide. Grandgenett, D.P. et al., *Proc. Natl. Acad. Sci. (USA)* 70:230–234 (1973); Moelling, K., *Virology* 62:46–59 (1974); Kotewicz, M.L., et al., *Gene* 35:249–258 (1985); and Roth, M.J., et al., *J. Biol. Chem.* 260:9326–9335 (1985). Little is known about the structure-functional relationship of these two activities, but such knowledge would be important both in understanding retroviral replication and in exploiting the enzyme as a recombinant DNA tool.

In the retrovirus life cycle, the RT DNA polymerase activity is responsible for transcribing viral RNA into double-stranded DNA. Varmus, H. (1982), in Weiss, R., et al. (eds.), *RNA Tumor Viruses*, Cold Spring Harbor Laboratory, pp. 410–423. The function of RNase H in replication is less clear, but it is thought to degrade genomic RNA during DNA synthesis to generate oligomeric RNA primers for plus-strand DNA synthesis, and to remove the RNA primers of both minus- and plus-strand DNA. Omer, C.A., et al., *Cell* 30:797–805 (1982); Resnick, R., et al., *J. Virol.* 51:813–821 (1984); Varmus, H. (1985), in Weiss, R., et al. (eds.), *RNA Tumor Viruses*, Cold Spring Harbor Laboratory, pp. 79–80.

The temporal relationship in vivo between DNA polymerization and RNA hydrolysis is not well defined. Furthermore, precisely how the two enzymatic activities are coordinated is not clear. Conditional mutations restricted to either DNA polymerase or RNase H would be invaluable in deciphering the events of retroviral replication. Unfortunately, conditional viral mutations in the RT gene invariably affect both activities. Lai, M.H.T, et al., *J. Virol.* 27:823–825 (1978); Moelling, K., et al., *J. Virol.* 22:370–378 (1979).

RT is used extensively in recombinant DNA technology to synthesize cDNA from mRNA. One major problem with cDNA synthesis is that the RNase H activity of RT degrades the mRNA template during first-strand synthesis. The mRNA poly(A)-oligo(dT) hybrid used as a primer for first-strand cDNA synthesis is degraded by RT RNase H. Thus, at the outset of cDNA synthesis, a competition is established between RNase H-mediated deadenylation of mRNA and initiation of DNA synthesis, which reduces the yield of cDNA product. Berger, S.L., et al., *Biochem.* 22:2365–2373 (1983). Furthermore, in some cases, the RNase H causes premature termination of DNA chain growth. Unfortunately, these events eliminate the potential for repeated copying of the RNA template.

Efforts to selectively inactivate RT RNase H with site-specific inhibitors have been unsuccessful (for review, see Gerard, G.F. (1983), in Jacob, S.T., (ed.), *Enzymes of Nucleic Acid Synthesis and Modification*, Vol. I, DNA Enzymes, CRC Press, Inc., Boca Raton, Fla., pp. 1–38). Attempts to physically separate the active centers of RT polymerase and RNase H activity by proteolysis have yielded a proteolytic fragment possessing only RNase H activity (Lai, M.H.T., et al., *J. Virol.* 25:652–663 (1978); Gerard, G.F., *J. Virol.* 26:16–28 (1978); and Gerard, G.F., *J. Virol.* 37:748–754 (1981)), but no corresponding fragment containing only polymerase activity has been isolated.

Computer analysis of the amino acid sequences from the putative gene products of retroviral pol genes has revealed a 150-residue segment at the carboxyl terminus that is homologous with the ribonuclease H of *E. coli* and a section close to the amino terminus which can be aligned with nonretroviral polymerases. Johnson, M.S., et al., *Proc. Natl. Acad. Sci. (USA)* 83:7648–7652 (1986). Based on these related amino acid sequences, Johnson et al. suggest that ribonuclease H activity should be situated at the carboxyl terminus, and the DNA polymerase activity at the amino terminus.

There have been a number of reports concerning the cloning of genes which encode RT and their expression in hosts. Weiss et al., U.S. Pat. No. 4,663,290 (1987); Gerard, G.F., *DNA* 5:271–279 (1986); Kotewicz, M.L., et al., *Gene* 35:249–258 (1985); Tanese, N., et al., *Proc. Natl. Acad. Sci. (USA)* 82:4944–4948 (1985); and Roth, M.J., et al., *J. Biol. Chem.* 260:9326–9335 (1985).

SUMMARY OF THE INVENTION

The invention relates to a gene which encodes reverse transcriptase having DNA polymerase activity and substantially no RNase H activity.

The invention also relates to a reverse transcriptase gene comprising the following DNA sequence:

```
                                                                          1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val
```

```
                                                                        1258
TCC ATA AAA CAA TAC CCC ATG TCA CAA GAA GCC AGA CTG GGG ATC AAG CCC CAC ATA CAG
Ser Ile Lys Gln Tyr Pro MET ser Gln Glu Ala Arg Leu Gly Ile Lys Pro His Ile Gln 1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu 1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn 1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu 1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg 1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile 1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe 1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu 1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly 1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala 1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp 1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln 1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu 2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp 2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu 2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly 2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu 2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu 2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala 2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His
```

```
                                                                    2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2512
CCG GCT ACG CTG CTC CCA CTG CCT GAG GAA GGG CTG CAA CAC AAC TGC CTT GAT
Pro Ala Thr Leu Leu Pro Leu Pro Glu Glu Gly Leu Gln His Asn Cys Leu Asp
``` or the degenerate variants thereof.

The invention also relates to a reverse transcriptase gene comprising the following DNA sequence:

```
                           .            .             .              .              .    1078
            ATG ACC CTA AAT ATA GAA GAT GAG CAT CGG CTA CAT GAG ACC TCA AAA GAG CCA GAT GTT
            MET Thr Leu Asn Ile Glu Asp Glu His Arg Leu His Glu Thr Ser Lys Glu Pro Asp Val

1138
            TCT CTA GGG TCC ACA TGG CTG TCT GAT TTT CTT CAG GCC TGG GCG GAA ACC GGG GGC ATG
            Ser Leu Gly Ser Thr Trp Leu Ser Asp Phe Pro Gln Ala Trp Ala Glu Thr Gly Gly MET

1198
            GGA CTG GCA GTT CGC CAA GCT CCT CTG ATC ATA CCT CTG AAA GCA ACC TCT ACC CCC GTG
            Gly Leu Ala Val Arg Gln Ala Pro Leu Ile Ile Pro Leu Lys Ala Thr Ser Thr Pro Val

1258
            TCC ATA AAA CAA TAC CCC ATG TCA CAA GAA GCC AGA CTG GGG ATC AAG CCC CAC ATA CAG
            Ser Ile Lys Gln Tyr Pro MET ser Gln Glu Ala Arg Leu Gly Ile Lys Pro His Ile Gln 1318
            AGA CTG TTG GAC CAG GGA ATA CTG GTA CCC TGC CAG TCC CCC TGG AAC ACG CCC CTG CTA
            Arg Leu Leu Asp Gln Gly Ile Leu Val Pro Cys Gln Ser Pro Trp Asn Thr Pro Leu Leu 1378
            CCC GTT AAG AAA CCA GGG ACT AAT GAT TAT AGG CCT GTC CAG GAT CTG AGA GAA GTC AAC
            Pro Val Lys Lys Pro Gly Thr Asn Asp Tyr Arg Pro Val Gln Asp Leu Arg Glu Val Asn 1438
            AAG CGG GTG GAA GAC ATC CAC CCC ACC GTG CCC AAC CCT TAC AAC CTC TTG AGC GGG CTC
            Lys Arg Val Glu Asp Ile His Pro Thr Val Pro Asn Pro Tyr Asn Leu Leu Ser Gly Leu 1498
            CCA CCG TCC CAC CAG TGG TAC ACT GTG CTT GAT TTA AAG GAT GCC TTT TTC TGC CTG AGA
            Pro Pro Ser His Gln Trp Tyr Thr Val Leu Asp Leu Lys Asp Ala Phe Phe Cys Leu Arg 1558
            CTC CAC CCC ACC AGT CAG CCT CTC TTC GCC TTT GAG TGG AGA GAT CCA GAG ATG GGA ATC
            Leu His Pro Thr Ser Gln Pro Leu Phe Ala Phe Glu Trp Arg Asp Pro Glu MET Gly Ile 1618
            TCA GGA CAA TTG ACC TGG ACC AGA CTC CCA CAG GGT TTC AAA AAC AGT CCC ACC CTG TTT
            Ser Gly Gln Leu Thr Trp Thr Arg Leu Pro Gln Gly Phe Lys Asn Ser Pro Thr Leu Phe 1678
            GAT GAG GCA CTG CAC AGA GAC CTA GCA GAC TTC CGG ATC CAG CAC CCA GAC TTG ATC CTG
            Asp Glu Ala Leu His Arg Asp Leu Ala Asp Phe Arg Ile Gln His Pro Asp Leu Ile Leu 1738
            CTA CAG TAC GTG GAT GAC TTA CTG CTG GCC GCC ACT TCT GAG CTA GAC TGC CAA CAA GGT
            Leu Gln Tyr Val Asp Asp Leu Leu Leu Ala Ala Thr Ser Glu Leu Asp Cys Gln Gln Gly 1798
            ACT CGG GCC CTG TTA CAA ACC CTA GGG AAC CTC GGG TAT CGG GCC TCG GCC AAG AAA GCC
            Thr Arg Ala Leu Leu Gln Thr Leu Gly Asn Leu Gly Tyr Arg Ala Ser Ala Lys Lys Ala 1858
            CAA ATT TGC CAG AAA CAG GTC AAG TAT CTG GGG TAT CTT CTA AAA GAG GGT CAG AGA TGG
            Gln Ile Cys Gln Lys Gln Val Lys Tyr Leu Gly Tyr Leu Leu Lys Glu Gly Gln Arg Trp 1918
            CTG ACT GAG GCC AGA AAA GAG ACT GTG ATG GGG CAG CCT ACT CCG AAG ACC CCT CGA CAA
            Leu Thr Glu Ala Arg Lys Glu Thr Val MET Gly Gln Pro Thr Pro Lys Thr Pro Arg Gln 1978
            CTA AGG GAG TTC CTA GGG ACG GCA GGC TTC TGT CGC CTC TGG ATC CCT GGG TTT GCA GAA
            Leu Arg Glu Phe Leu Gly Thr Ala Gly Phe Cys Arg Leu Trp Ile Pro Gly Phe Ala Glu
```

```
                                                                 2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp

2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC AAT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC AAT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT AAT TCC
Pro Ala Thr Leu Leu Pro Leu Pro Glu Glu Gly Leu Gln His Asn Cys Leu Asp Asn Ser

2530
CGC TTA ATT AAT
Arg Leu Ile Asn
``` or the degenerate variants thereof.

The invention also relates to the vectors containing the gene of the invention, hosts transformed with the vectors of the invention, and the reverse transcriptase expressed by the transformed hosts of the invention.

The invention also relates to a fusion protein comprising a polypeptide having RNA-dependent DNA polymerase activity and substantially no RNase H activity and a second peptide selected from polypeptide proteins which stabilize the fusion protein and hydrophobic leader sequences.

The invention also relates to a method of producing reverse transcriptase having DNA polymerase activity and substantially no RNase H activity, comprising culturing transformed hosts of the invention under conditions which produce reverse transcriptase, and isolating the reverse transcriptase so produced.

The invention also relates to a method of preparing cDNA from mRNA comprising contacting mRNA with a polypeptide having RNA-dependent DNA polymerase activity and substantially no RNase H activity, and isolating the cDNA so produced.

The invention also relates to a kit for the preparation of cDNA from mRNA comprising a carrier being compartmentalized to receive in close confinement therein one or more containers, wherein
  (a) a first container contains reverse transcriptase having DNA polymerase activity and substantially no RNase H activity;
  (b) a second container contains a buffer and the nucleoside triphosphates;
  (c) a third container contains oligo(dT)primer; and
  (d) a fourth container contains control RNA.

The invention is related to the discovery that portions of the RT gene can be deleted to give a deletion mutant having DNA polymerase activity but no detectable RNase H activity. This purified mutant RT lacking RNase H activity can be used to effectively synthesize cDNA from mRNA.

Figure 1:
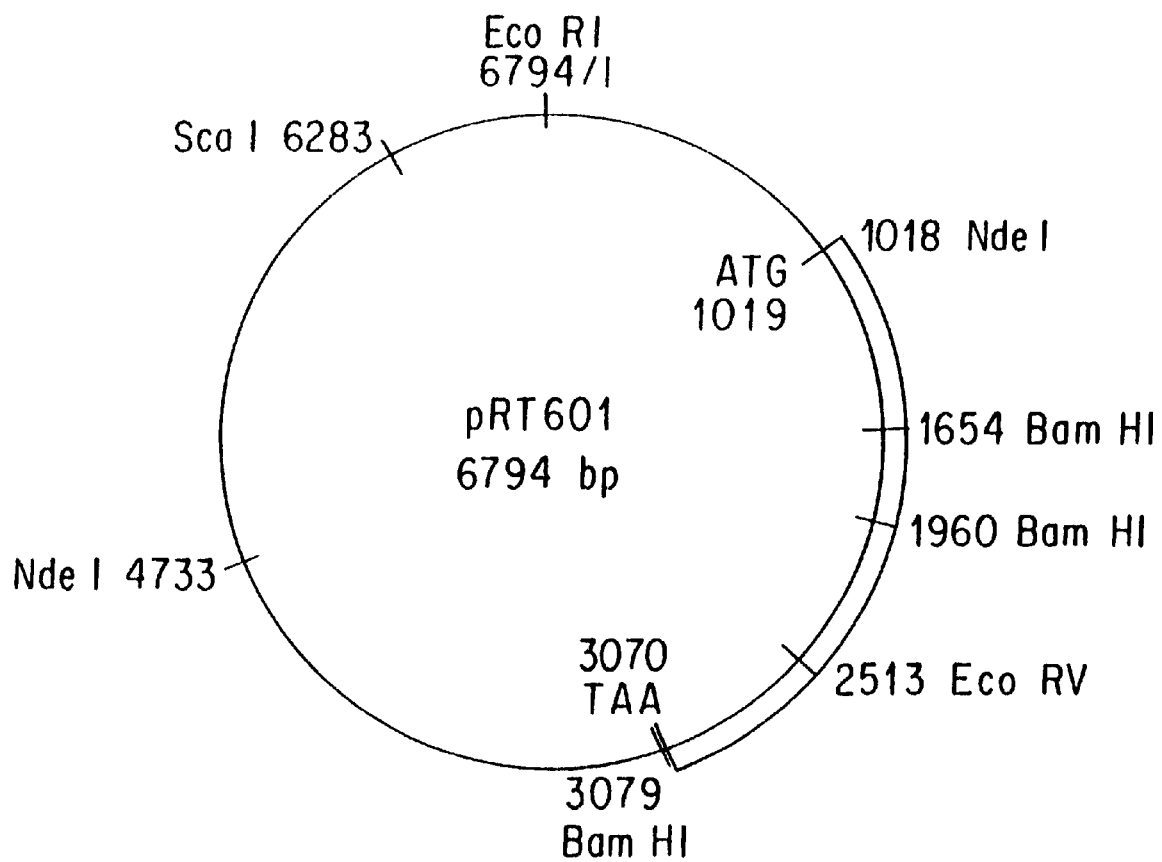
FIG. 1. This figure depicts the restriction map of plasmid pRT601. The M-MLV RT gene extends from position 1,019 to 3,070.

Aliquots were removed from reaction mixtures containing no enzyme (−E) or 200 units of RT at the times indicated (in min). The minus enzyme control was incubated for 60 min. Samples were electrophoresed as described in Materials and Methods. A 1 kb ladder was used as marker (M).

FIGS. 6A, 6B and 6C depict the DNA sequence which encodes reverse transcriptase having DNA polymerase activity and substantially no RNase H activity. Also shown is the corresponding amino acid sequence.

DESCRIPTION OF THE PREFERRED EMBODIMENTS

The invention relates to the production of reverse transcriptase having DNA polymerase activity and substantially no RNase H activity, using recombinant DNA techniques.

Recombinant plasmids constructed as described herein provide reverse transcriptase for use in recombinant DNA technology to synthesize cDNA from mRNA without the problem associated with RNase H activity which degrades mRNA template during first-strand synthesis.

By the terms "substantially no RNase H activity" is intended reverse transcriptase purified to near homogeneity and having an RNase H activity of less than 0.001 pmoles $[^3H](A)_n$ solubilized per μg protein with a $[^3H](A)_n \cdot (dT)_n$ substrate in which the $[^3H](A)_n$ has a specific radioactivity of 2,200 cpm/pmole. RNase H activities of this specific activity or less allows the preparation of cDNA without significant degradation of the mRNA template during first-strand synthesis.

By the terms "degenerate variants" is intended cloned genes having variations of DNA sequence, but which encode the same amino acid sequence.

The reverse transcriptase gene (or the genetic information contained therein) can be obtained from a number of different sources. For instance, the gene may be obtained from eukaryotic cells which are infected with retrovirus, or from a number of plasmids which contain either a portion of or the entire retrovirus genome. In addition, messenger RNA-like RNA which contains the RT gene can be obtained from retroviruses. Examples of sources for RT include, but are not limited to, Moloney murine leukemia virus (M-MLV); human T-cell leukemia virus type I (HTLV-I); bovine leukemia virus (BLV); Rous Sarcoma Virus (RSV); human immunodeficiency virus (HIV); yeast, including Saccharomyces, Neurospora, Drosophila; primates; and rodents. See, for example, Weiss et al., U.S. Pat. No. 4,663,290 (1987); Gerard, G.R., *DNA* 5:271–279 (1986); Kotewicz, M.L., et al., *Gene* 35:249–258 (1985); Tanese, N., et al. *Proc. Natl. Acad. Sci. (USA)* 82:4944–4948 (1985); Roth, M.J., et al., *J. Biol. Chem.* 260:9326–9335 (1985); Michel, F., et al., *Nature* 316:641–643 (1985); Akins, R.A., et al., *Cell* 47:505–516 (1986), *EMBO J.* 4:1267–1275 (1985); and Fawcett, D.F., *Cell* 47:1007–1015 (1986).

RT proviral DNA can be isolated using standard isolation techniques. The DNA is cleaved into linear fragments, any one of which may contain the genes which encode RT. Such fragmentation can be achieved using enzymes which digest or cleave DNA, such as restriction enzymes which cleave DNA as specific base sequences. After the linear DNA fragments are generated, they are separated according to size by standard techniques. Such recombinant DNA techniques may be performed as described by Maniatis, T., et al., *Molecular Cloning: A Laboratory Manual*, Cold Spring Harbor Laboratory, Cold Spring Harbor, N.Y. (1982).

Identification of the DNA fragment which contains the gene may be accomplished in a number of ways. For example, it is possible to sequence the DNA fragments (Maxam and Gilbert, *Methods in Enzymology* 64:499 (1980); Messing, J., *Meth. in Enz.* 101C:20 (1983)) to identify which fragment contains the reverse transcriptase gene. Alternatively, hybridization techniques (Southern, *J. Mol. Biol.* 98:503 (1975)) using a labeled (e.g., radioactively labeled) DNA probe may be employed.

The fractions containing the desired DNA are pooled, ligated into a suitable vector, and used to transform a host. Screening for transformed hosts containing the RT gene may be accomplished by, for example, the method disclosed by Gerard et al., *Biochem.* 13:1632–1641 (1974) or by Gerard et al., *J. Virol.* 15:785–797 (1975). Alternatively, clones containing reverse transcriptase may be identified by hybridization with complementary labeled DNA.

An alternative to isolating the reverse transcriptase gene from a retroviral proviral DNA is to make cDNA to the mRNA-like RNA which codes for reverse transcriptase. To this end, mRNA-like RNA coding for reverse transcriptase is isolated from retrovirus. By standard techniques, the isolated mRNA is then converted into cDNA using reverse transcriptase. The cDNA can then be inserted into a plasmid vector in a conventional manner.

The choice of a suitable vector depends on a number of considerations known to one of ordinary skill in the art, such as the size of the fragment, nature of the host, number and position of restriction sites desired, and the selection marker and markers desired. Such vectors may include replicon and control sequences from species compatible with a host cell (see Maniatis et al., supra). Expression of the RT genes may also be placed under control of other regulatory sequences homologous or heterologous to the host organism in its untransformed state. For example, lactose-dependent *E. coli* chromosomal DNA comprises a lactose or lac operon which mediates lactose utilization by elaborating the enzyme β-galactosidase. The lac control elements may be obtained from bacteriophage lambda plac 5, which is infectious for *E. coli*. The lac promoter-operator system can be induced by IPTG.

Other promoter-operator systems or portions thereof can be employed as well. For example, galactose, alkaline phosphatase, tryptophan, xylose, tac, lambda pL, lambda pR and the like can be used. Once the vector or DNA sequence containing the constructs has been prepared, the vectors may be introduced into an appropriate host. Various techniques may be employed such as protoplast fusion, $CaCl_2$, calcium phosphate precipitation, electroporation, or other conventional DNA transfer techniques. The vectors may then be introduced into a second host by similar transfer methods, and also by cell to cell transfer methods such as conjugation. This cell-to-cell transfer may be accomplished using known techniques which depend upon the nature of the transferer bacterium, the recipient bacterium, and the cloning vector used to propagate the RT DNA. The transfer may require the use of a helper plasmid. See, for example, Ditta, G., et al., *Proc. Natl. Acad. Sci. (USA)* 77:7347–7351 (1980).

RT genes having DNA polymerase activity and substantially no RNase H activity may be obtained by deletion of deoxyribonucleotides at the 3′ end of the gene which encode the portion of the polypeptide having RNase H activity. Deletions of the RT gene may be accomplished by cutting the plasmid at selected restriction sites within the RT gene and discarding the excised fragment. Further deletion of consecutive deoxyribonucleotides may be accomplished by treating the fragment with an exonuclease. The DNA ends may then be joined in such a way that the translation reading frame of the gene is maintained. The plasmid thus obtained may then be used to transform hosts which may then be screened for altered RT activity. RT RNase H activity may be assayed according to Gerard et al., *J. Virol.* 15:785–797 (1975). DNA polymerase activity may be assayed according to Gerard et al., *Biochem.* 13:1632–1641 (1974). Clones having DNA polymerase activity and substantially no RNase H activity may be used to prepare RT with altered activity.

According to these methods, the portion of the RT gene derived from M-MLV which encodes DNA polymerase was localized to about 1495 base pairs (about 1018 to about 2512) as shown in FIG. 6. The protein expressed by this gene has about 503 amino acids (FIG. 6). This protein has DNA polymerase activity and substantially no RNase H activity.

The invention also relates to fusion proteins which comprise the reverse transcriptase of the invention. Such fusion proteins may comprise, for example, a carrier protein which has a leader sequence of hydrophobic amino acids at the amino terminus of the reverse transcriptase. This carrier protein is normally excreted through the membrane of the cell within which it is made. By cleavage of the hydrophobic leader sequence during excretion, a means is provided for producing reverse transcriptase which can be recovered either from the periplasmic space or the medium in which the bacterium is grown. The use of such a carrier protein allows isolation of reverse transcriptase without contamination by other proteins within the bacterium, and achieves production of a form of reverse transcriptase having greater stability by avoiding the enzymes within the bacterial cell which degrade foreign proteins. The DNA and amino acid sequences for such hydrophobic leader sequences, as well as methods of preparing such fusion proteins are taught, for example, by Gilbert et al., U.S. Pat. No. 4,411,994 (1983).

It is also possible to prepare fusion proteins comprising the reverse transcriptase of the invention which is substituted at the amino or carboxy termini with polypeptides which stabilize or change the solubility of the reverse transcriptase. An amino-terminal gene fusion which encodes reverse transcriptase, having both DNA polymerase and RNase activity, and trpE taught, for example, by Tanese, N. et al., *Proc. Nat'l. Acad. Sci.* 82:4944–4948 (1985). A carboxy-terminal gene fusion which encodes reverse transcriptase and part of the plasmid pBR322 tet gene is taught, for example, by Kotewicz, M., et al., *Gene* 35:249–258 (1985) and Gerard, G., *DNA* 5:271–279 (1986).

The transformed hosts of the invention may be cultured under protein producing conditions according to any of the methods which are known to those skilled in the art.

The reverse transcriptase having DNA polymerase activity and substantially no RNase activity may be isolated according to conventional methods known to those skilled in the art. For example, the cells may be collected by centrifugation, washed with suitable buffers, lysed, and the reverse transcriptase isolated by column chromatography, for example, on DEAE-cellulose, phosphocellulose (see Kotewicz et al., *Gene* 35:249–258 (1985)) or other standard isolation and identification techniques using, for example, polyribocytidylic acid-agarose, or hydroxylapatite or by electrophoresis or immunoprecipitation.

The reverse transcriptase so produced may be used to prepare cDNA from RNA by, for example, hybridizing an oligo(dT) primer or other complementary primers with the mRNA. The synthesis of a complete cDNA may be accomplished by adding the reverse transcriptase and all four deoxynucleoside triphosphates. Using the reverse transcriptase produced by the present invention allows for the preparation of cDNA from mRNA without concomitant degradation of the mRNA which results in incomplete cDNA synthesis. The resulting RNA-DNA hybrid may be treated, for example, with alkali or RNase H to selectively hydrolyze the RNA to leave cDNA which may be converted to double-stranded form in a second DNA reaction catalyzed by reverse transcriptase or other DNA polymerase. See Old, R.W., et al., *Principals of Gene Manipulation,* second edition, Studies in Microbiology, Vol. 2, University of California Press, p. 26 (1981).

The reverse transcriptase of the invention is ideally suited for incorporation into a kit for the preparation of cDNA from RNA. Such a kit may comprise a carrier means being compartmentalized to receive a close confinement therein, one or more container means, such as vials, tubes, and the like, each of said container means comprising one of the separate elements of the method used to prepare cDNA from RNA. For example, there may be provided a container means containing reverse transcriptase having DNA polymerase activity and substantially no RNase H activity, in solution. Further container means may contain suitable buffers, substrates for DNA synthesis such as the deoxynucleoside triphosphate, oligo(dT) primer, and control RNA for use as a standard.

The reverse transcriptase may be present in the solution at a concentration of 200 units/ml to 400 units/ml. The deoxynucleoside triphosphases may be present either in lyophilized form or as part of a buffer at a concentration of 0.5 mM to 2 mM. A suitable buffer, present at 5 times the final concentration of use, includes 250 mM Tris-HCl (pH 7.5 to 8.3), 375 mM KCl, 15 mM $MgCl_2$, and 50 mM dithiothreitol. The oligo (dT) may be present at a concentration of 5 μg/ml to 20 μg/ml. Control RNA, such as 2.3 kb control RNA, may be present at a concentration of 10 μg/ml to 20 μg/ml.

The following examples are illustrative but not limiting of the methods and compositions of the present invention. Any suitable modifications and adaptations which are obvious to one of ordinary skill in the art in recombinant DNA techniques are within the spirit and scope of the present invention.

EXAMPLES

MATERIALS AND METHODS

Plasmids and Bacterial Strains

For deletion analysis of RT, a clones of M-MLV RT was constructed to overproduce stable RT in *Escherichia coli*, pRT601 (FIG. 1). Gerard, G.F., et al., *DNA* 5:271–279 (1986). It is a pBR322 replicon containing the strong lambda leftward promoter, pL, and the ribosome binding site of the lambda cII gene. (Higher copy number derivatives of pBR322, such as pUC plasmids, can also be used.) The coding sequence for the RT gene was carefully engineered into this plasmid to produce a protein with the amino terminus of the viral protein, and a carboxy terminus similar to the viral enzyme. Gerard, G.F., supra.

Two bacterial strains were used to propagate clones and express RT: K802 (Maniatis, T., et al., (1982), *Molecular Cloning: A Laboratory Handbook,* pp. 504–505, Cold Spring Harbor Laboratory, Cold Spring Harbor, N.Y.), made lysogenic for lambda cIindlts850 Sam7, and N4830 (Gottesman, M.E., et al., *J. Mol. Biol.* 140:57–75 (1980)), which contains a deleted a cryptic lambda prophage expressing the temperature sensitive cI allele indlts857. Bacteria were grown in super broth (SB) containing 2% tryptone, 1% yeast extract, 0.1% NaCl, pH 7.5, and 50 μg/ml ampicillin.

Plasmid Construction

Standard procedures for plasmid construction were performed as described previously (Kotewicz, M.L., et al., *Gene* 35:249–258 (1985); Gerard, G.F., et al., *DNA* 5:271–279 (1986)).

Temperature Induction of *E. coli* Carrying pRT601 and Its Derivatives

Cultures of bacteria were grown in SB broth overnight at 32° C. and diluted 1:20 in fresh SB in the morning. The cells were grown at 32° C. until the $A_{590}$ was 0.8, and were induced by swirling in a 65° C. water bath until the temperature reached 42° C. Induction was continued for 30 minutes in a shaking water bath at 42° C., and then the cultures were incubated at 37° C. and grown an additional 30 minutes.

Preparation of Cell Extracts

Unless otherwise noted, all operations were performed at 4° C. Pelleted cells from one ml of culture were washed, lysed, and centrifuged as described previously (Kotewicz, M.L., supra). Supernatants were removed and assayed for RNase H and DNA polymerase activity.

Enzymes Assays

RT DNA polymerase activity in extracts was assayed specifically by using poly(2'-O-methylcytidylate).oligodeoxyguanylate $[(Cm)_n.(dG)_{12-18}]$ (Gerard, G.F., et al., *DNA* 5:271–279 (1986), eliminating interference from cellular DNA polymerases. To establish DNA polymerase specific activities of purified RT preparations, activity was assayed with $(A)_n.(dT)_{12-18}$ (Houts, G.E., et al., *J. Virol.* 29:517–522 (1979) as described by Gerard, G.F., et al., *DNA* 5:271–279 (1986). One unit of DNA polymerase activity is the amount of enzyme that incorporates one nmole of deoxynucleoside monophosphate into acid insoluble product at 37° C. in 10 min.

RNase H activity in crude extracts and purified enzyme was assayed in reaction mixtures (50 μl) containing 50 mM Tris-HCl (pH 8.3), 2 mM $MnCl_2$, 1 mM dithiothreitol, and $[^3H](A)_n.(dT)_n$ (5 μM $[^3H](A)_n$, 35 cpm/p-mole; 20 μM $(dT)_n$). Reactions were incubated at 37° C. for 20 min and were stopped by adding 10 μl of tRNA (1 mg/ml) and 20 μl of cold 50% TCA. After 10 minutes on ice, the mixture was centrifuged for 10 minutes in an Eppendorf centrifuge. Forty μl of the supernatant was counted in aqueous scintillant. One unit of RNase H activity is the amount of enzyme required to solubilize one mole of $[^3H](A)_n$ in $[^3H](A)_n.(dT)_n$ in 10 min at 37° C.

Synthesis of Poly(A)-Tailed RNA

Synthetic 2.3 kb and 6.2 kb RNAs containing a 19 nucleotide poly(A) tail at the 3' end were synthesized with T7 RNA polymerase from Xba I-cut pJD2.3 and Hind III-cut pHL3X, respectively. Reaction mixtures (0.3 ml) contained 40 mM Tris-HCl (pH 8.0), 8 mM $MgCl_2$, 2 mM spermidine-HCl, 5 mM dithiothreitol, 0.4 mM each of CTP, UTP, GTP, and ATP, 20 μg/ml DNA, and 2,000 units/ml T7 RNA polymerase. Uniformly labeled RNA was synthesized with all four $[\alpha-^{32}P]NTPs$, each at 0.4 mM and 250 cpm/pmole. After 1 hr incubation at 37° C., the RNA product was phenol extracted, ethanol precipitated, and purified by oligo(dT)-cellulose chromatography to ensure the presence of a poly (A) tail.

Conditions for cDNA Synthesis

When assessing the effect of cDNA synthesis upon the integrity of template RNA, reaction mixtures (50 μl) contained 50 mM Tris-HCl (pH 8.3), 75 mM KCl, 3 mM $MgCl_2$, 10 mM dithiothreitol, 0.5 mM each dATP, dGTP, and dTTP, 0.5 mM $[^3H]dCTP$ (200 cpm/pmol), 50 μg/ml $(dT)_{12-18}$, 20 μg/ml 2.3 kb $[^{32}P]$labeled RNA, and 4,000 units/ml RT. The reactions were incubated at 37° C. and duplicate 2.5 μl aliquots were removed at 0, 1, 5, 10, 30, and 60 min. One aliquot was precipitated onto glass fiber filters using TCA to determine the amount of cDNA synthesized, and the other aliquot was prepared for glyoxal gel analysis. Carmichael, G.G., et al., *Method. Enzymol.* 65:380–391 (1980). The glyoxalated RNA was fractionated on a 1% agarose gel, dried, and autoradiographed. In some cases, 10 units of *E. coli* RNase H were added to the reaction mixture after 60 min and the incubation continued for 10 more min before aliquots were taken.

When measuring the ability of RT to synthesize a cDNA copy of long RNA, reaction mixtures (10 μl) contained the same buffer and salts, 0.5 mM each of dATP, dGTP, dTTP, and $[\alpha-^{32}P]dCTP$ (600 cpm/pmole), 50 μg/ml actinomycin D, 50 μg/ml $(dT)_{12-18}$, 100 μg/ml 6.2 kb poly(A)-tailed RNA, and 20,000 units/ml RT. After 1 hr at 37° C., the product in an aliquot (1 μl) was precipitated with TCA, counted, and the remaining DNA size fractionated on an alkaline 1.4% agarose gel according to McDonnel, M.W, et al., *J. Mol. Biol.* 110:119–146 (1977).

Purification of RT

Cells were grown to an $A_{590}$ of 3 in TYN and ampicillin medium (Gerard, G.F., et al., *DNA* 5:271–279 (1986)) at 30° C., induced at 43° C. for 45 min, and then grown at 36° C. for 3.5 hr before harvesting. RT was extracted from 100 g of cells as described (Gerard, G.F., supra) with the following exceptions. RT was precipitated by addition of solid $(NH_4)_2SO_4$ to 40% saturation. The $(NH_4)_2SO_4$ pellet was dissolved in 50 ml of 20 mM Tris-HCl (pH 7.5), 1 mM EDTA, 0.1 M NaCl, 5% glycerol, 1 mM dithiothreitol, and 0.01% n-octyl-β-D-glucopyranoside, the suspension was clarified by centrifugation at 10,000×g for 10 min, and the supernatant was desalted on a 320 ml (5×16 cm) Sephadex G-25 column run in buffer A (20 mM Tris-HCl, pH 7.5, 1 mM dithiothreitol, 1 mM EDTA, 5% glycerol, 0.01% NP-40) plus 0.1 M NaCl. After phosphocellulose chromatography, the RT peak was pooled, diluted with an equal volume of buffer A, and chromatographed on a 21-ml heparin-agarose column (1.5×12 cm) equilibrated in buffer A plus 0.1 M NaCl. The RT peak from the heparin-agarose column was chromatographed on a Mono-S HR 5/5 column equilibrated in buffer A (Gerard, G.F., supra).

RESULTS

Construction of Reverse Transcriptase Gene Deletions

Figure 2:
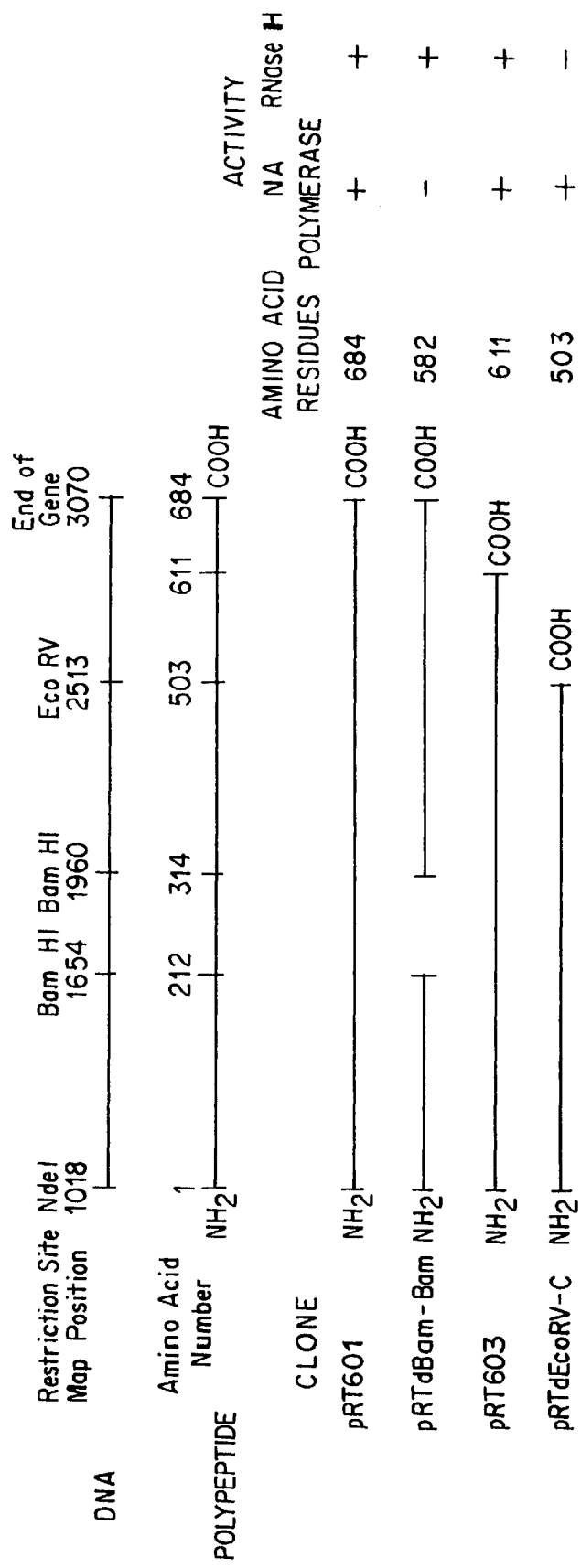
FIG. 2. This figure depicts schematic representation of pRT601 and related plasmids, and the enzymatic activities and predicted structure of the M-MLV RT protein coded by each plasmid.

Deletions of the M-MLV RT gene were constructed by cutting pRT601 (FIG. 1) at selected restriction sites within the RT gene, discarding the excised fragment, and joining the DNA ends in such a way that the translation reading frame of the gene was maintained. pRTdBam-Bam was constructed by deleting the Bam HI fragment between nucleotide positions 1,654 and 1,960 (FIGS. 1 and 2). Ligation of the Bam HI half sites at positions 1,654 and 1,960 maintained the translation reading frame across the site.

A deletion at the carboxy terminus of M-MLV RT (pRTdEcoRV-C) was constructed by deleting all of the 3' end of the gene downstream of the Eco RV site at position 2,513 (FIGS. 1 and 2). To construct pRTd-EcoRV-C, a Sca I (position 6,238) to Eco RV (position 2,513) fragment of pRT601 containing the 5' portion of the RT gene was ligated to a Sca I-Eco RI fragment derived from plasmid pBRT (Gerard, G.F., supra). The 3,211 base pair pBRT Sca I-Eco RI fragment contained the pBR322 origin of replication and a universal translation terminator sequence just inside the Eco RI site. The Eco RI site was repaired with DNA polymerase I Klenow fragment before ligation.

The plasmid of pRTdEcoRV-C was deposited in E. coli under the terms of the Budapest Treaty at the American Type Culture Collection (ATCC), Rockville, Md., and given accession number 67555.

pRT603 was constructed as described (Gerard, G.R., supra) which encodes an RT that contains 73 fewer amino acids than pRT601, all deleted from the carboxy terminus (FIG. 2).

DNA Polymerase and RNase H Levels in Cells Bearing Deletion Plasmids

Alteration of as little as 3 amino acids at the carboxy end of M-MLV RT can influence markedly the stability of the protein in E. coli (Gerard, G.F. supra). This must be taken into consideration in making correlations between cloned RT deletions and enzymatic activities in E. coli extracts. Both DNA polymerase and RNase H activity must be assayed and relative enzyme levels compared. For example, pRT603 codes for an RT with 73 fewer amino acids at the carboxy terminus than pRT601 RT (Gerard, G.F., supra; FIG. 2). The level of DNA polymerase activity in E. coli extracts of pRT603 RT is reduced 5 fold relative to pRT601. (Gerard, G.F. supra). However, the DNA polymerase and RNase H specific activities of purified pRT601 and pRT603 RT are comparable (Table 2). The reduced DNA polymerase activity in E. coli extracts of pRT603 RT is not due to a selective effect of the deletion on DNA polymerase activity, but rather to a reduction in the stability of pRT603 RT relative to pRT601 RT in cells ($t_{1/2}$ of 7 min versus 33 min) (Gerard, G.F. supra). Therefore, deletions within 70 amino acids of the RT carboxy terminus do not affect either RNase H or DNA polymerase activity.

In contrast, the DNA polymerase activity of pRTdBam-Bam RT was eliminated totally without affecting RNase H activity (Table 1) by the deletion of 102 amino acid residues between amino acids 212 and 314 (FIG. 2). Introduction of a more extensive deletion of 180 amino acids at the carboxy end of RT in pRTdEcoRV-C RT (FIG. 2) yielded extracts with RT DNA polymerase levels unchanged compared to pRT601 extracts, but with RNase H levels reduced 7.5 fold (Table 1). The residual RNase H activity in pRTdEcoRV-C extracts could be due to E. coli RNase H, the 5'→3' exonuclease of DNA polymerase I, or a small amount of residual RT-coded RNase H activity. To resolve this issue, pRTdEcoRV-C RT was purified and compared to RT encoded by pRT601.

Purification and Properties of pRTdEcoRV-C RT

Figure 3:
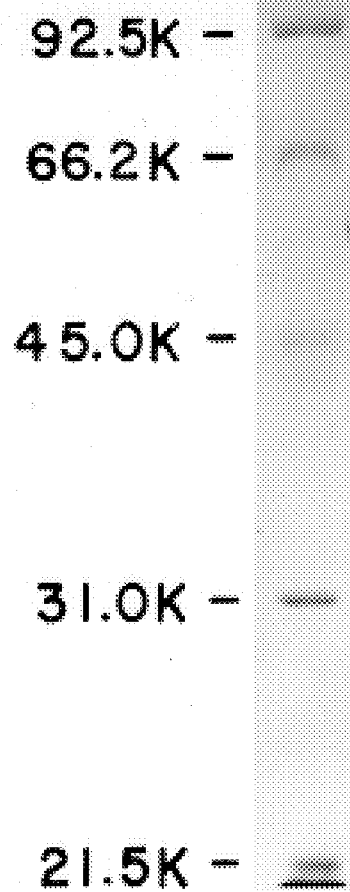
FIG. 3. This figure depicts an SDS-polyacrylamide gel of M-MLV RT. pRTdEcoRV-C RT (A) and pRT601 RT (B) (3 µg of each) were run on an SDS 10% polyacrylamide gel (Laemmli, U.K., Nature 227:680–685 (1970)). The gel was stained with Coomassie blue. Lane M contained $M_r$ standards.

M-MLV reverse transcriptase encoded by pRTdEcoRV-C, pRT601, and pRT603 were purified as described in Materials and Methods. A summary of the purification of pRTdEcoRV-C RT is presented in Table 3. Three column steps produced a nearly homogeneous mutant enzyme with the same DNA polymerase specific activity as pRT601 RT with the template-primer $(Cm)_n \cdot (dG)_{12-18}$ (Table 2). With $(A)_n \cdot (dT)_{12-18}$, the mutant enzyme had one-fourth the DNA polymerase activity of pRT601 RT (Table 2). RNase H activity of purified pRTdEcoRV-C RT was undetectable using $[^3H](A)_n \cdot (dT)_n$ as the substrate. Most RNase H activity in extracts was eliminated from mutant RT by precipitation of the enzyme with 40% $(NH_4)_2SO_4$ (Table 3). Under these conditions, DNA polymerase I remains soluble (Richardson, C., et al., J. Biol. Chem. 239:222–230 (1964)), as does most of the RNase H activity in the extract. As judged by SDS-polyacrylamide gel electrophoresis, pRTdEcoRV-C RT purified through the Mono-S column was greater than 90% pure and had a molecular weight of 56,000 (FIG. 3), consistent with the molecular weight (57,000) predicted by the DNA sequence.

Figure 4:
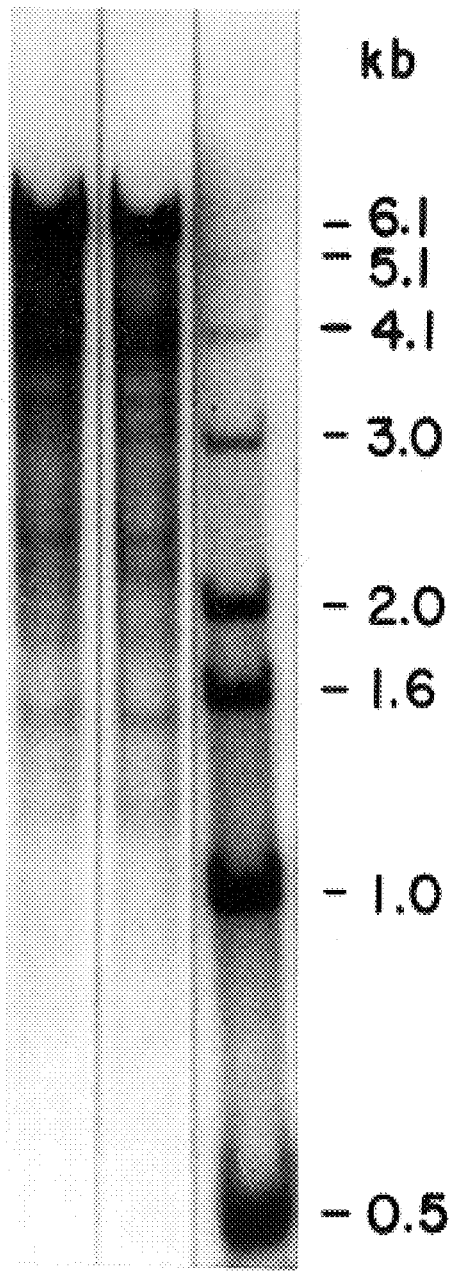
FIG. 4. This figure depicts an autoradiogram of $^{32}$P-labeled cDNA synthesized from 6.2 kb RNA (Materials and Methods) by pRTdEcoRV-C RT (A) or pRT601 RT (B). A 1 kb ladder was used as a standard (C). Electrophoresis was performed on an alkaline 1.4% agarose gel (McDonnel, M.W., et al., J. Mol. Biol. 110:119–146 (1977)).

A number of enzymatic properties of purified pRTdEcoRV-C RT and pRT601 RT were compared and were found to be similar. These included half life at 37° C., monovalent and divalent metal ion optima, fidelity of dNTP incorporation with homopolymer templates, and insensitivity to stimulation by polyanions. The abilities of the two enzymes to synthesize heteropolymeric DNA were also compared. FIG. 4 shows that pRTdEcoRV-C RT catalyzed the synthesis of full-length cDNA from 6.2 kb RNA more efficiently than pRT601 RT. The amount of cDNA synthesized from 1 μg of RNA was 0.28 μg (34% full-length) and 0.24 μg (24% full-length) with pRTdEcoRV-C RT and pRT601 RT, respectively.

Figure 5A:
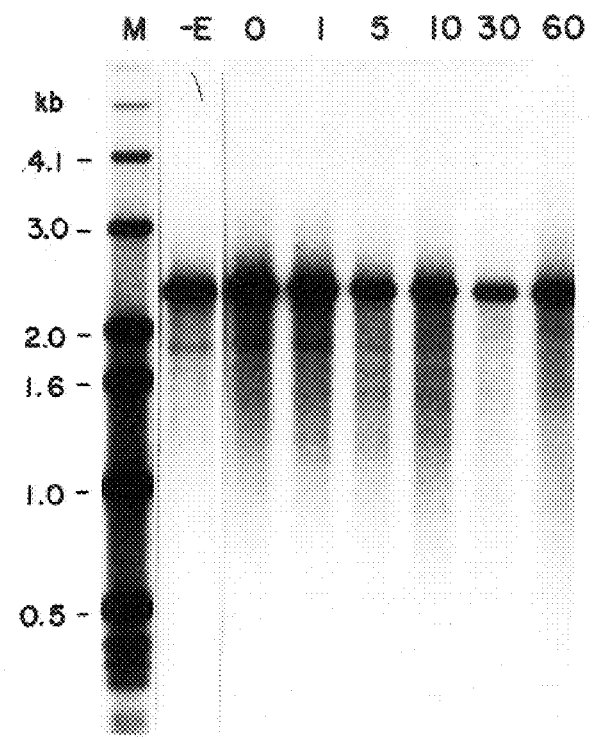
FIGS. 5A and 5B depict autoradiograms of $^{32}$P-labeled 2.3 kb poly(A)-tailed RNA after oligo(dT)primed cDNA synthesis catalyzed by pRTdEcoRV-C RT or pRT601 RT.
Figure 5B:
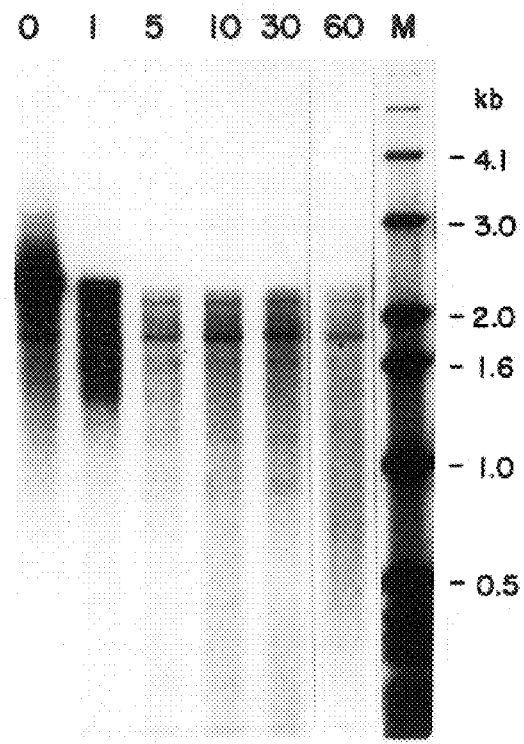

To confirm that pRTdEcoRV-C RT completely lacked RNase H activity, the integrity of a uniformly $^{32}$P-labeled RNA template after conversion to hybrid form during RT-catalyzed DNA synthesis was examined. FIG. 5 shows that with pRT601 RT, the full-length 2.3 kb RNA template was degraded totally after 5 min of synthesis. In contrast, with pRTdEcoRV-C RT the RNA was intact even after 60 min. The amount of cDNA synthesized after 60 min from 1 μg of RNA was 0.67 and 0.76 μg with pRT601 and pRTdEcoRV-C RT, respectively. When 10 units of E. coli RNase H were added to the pRTdEcoRV-C RT reaction after 60 min of incubation, all of the RNA was degraded, confirming the hybrid state of the RNA. In addition, 15 μg (1,200 units) of pRTdEcoRV-C RT solubilized no radioactivity from a $[^3H](A)_n \cdot (dT)_n$ substrate in which the $[^3H](A)_n$ had a specific activity of 2,200 cpm/pmole (Materials and Methods).

Experiments with a frameshift mutant of MLV producing a 47 K RT molecule truncated at the carboxy terminus (Levin, J.G. et al., J. Virol. 51:470–478 (1984)) and with antibodies to synthetic peptides modeled to Rous sarcoma virus pol gene sequences (Grandgenett, D. et al., J. Biol. Chem. 260:8243–8249 (1985)) suggest the RNase H activity of RT resides within the amino-terminal portion of the molecule. Conversely, the extensive homology found between the amino acids of E. coli RNase H and the 153-residue segment at the carboxy-terminal end of M-MLV RT (Johnson, M.S. et al. Proc. Natl. Acad. Sci (USA) 83:7648–7652 (1986)) suggests the RNase H activity resides within the carboxy-terminal portion of RT.

By deleting large segments (100 to 200 codons) of the M-MLV RT gene, the regions within the RT molecule responsible for DNA polymerase and RNase H activity have been identified. DNA polymerase was mapped to the amino half of the molecule, and RNase H to within 200 amino acids of the carboxy end, confirming the predictions based upon amino acid homology (Johnson, M.S. et al., supra). In this context, the results with one RT clone, pRT603 (FIG. 2), are of interest. The RT protein encoded by pRT603 is missing the carboxy half of the 153 amino acid segment of RT homologous to E. coli RNase H, which includes 20 of 48 homologous amino acids. Yet, pRT603 RT has normal levels of RNase H activity. These missing, homologous residues apparently are not required for catalysis, and might serve a nucleic acid binding or structural role. Consistent with the latter, a single amino acid change at a position 12 residues from the carboxy end of E. coli RNase H produces a 10-fold reduction in RNase H specific activity (Kanaya, S. et al., J. Bacteriol. 154:1021–1026 (1983)). This reduction appears to be the result of altered protein conformation (Kanaya, S. et al., supra).

If the RT polymerase and nuclease active sites reside on separate structural domains, it should be possible theoretically to isolate two separate protein fragments, each with a single activity. A 24 K to 30 K proteolytic fragment of RT possessing only RNase H activity has been isolated (Lai, M.H.T. et al., J. Virol. 25:652–663 (1978); Gerard, G.F., J. Virol. 26:16–28 (1978); Gerard, G.F., J. Virol. 37:748–754 (1981)), but unfortunately, the location of this RNase H fragment in the parent RT polypeptide has not been established, and no analogous DNA polymerase containing fragment has ever been found. The results presented here show that of the 684 amino acids in pRT601 RT, residues between amino acid 212 and 314 are required for DNA polymerase activity, and residues between amino acid 503 and 611 are required for RNase H activity. They also demonstrate for the first time that the RT DNA polymerase activity can exist independently of RNase H activity on an RT protein fragment. Purified pRTdEcoRV-C RT appeared to be totally devoid of RNase H activity, based upon two sensitive assays, and to have full DNA polymerase activity. However, these results do not rule out the possibility that the two active centers share a portion(s) of the RT molecule.

Demonstration of a separate structural domain for the RNase H active center was attempted by constructing two amino-terminal deletion derivatives of pRT601. The first derivative contained sequences for the Eco RV site at position 2513 to the 3' end of the RT gene (see FIG. 2), and the second contained sequences from an Nco I site at position 2302 to the 3' end of the RT gene. Unfortunately, neither clone produced detectable RNase H activity in E. coli crude extracts. Such negative results are difficult to interpret because the proteins might be unable to fold in an active form, or might be extremely labile.

Deletion of the carboxy-terminal one-fourth of the M-MLV RT molecule did not disrupt the ability of the protein to fold in an active conformation. pRTdEcoRV-C RT copied heteropolymeric RNA more efficiently than intact RT. Yields of cDNA from 1 μg of 2.3 kb and 6.2 kb RNA were 0.76 μg (50% full-length) and 0.28 μg (34% full-length), respectively. Also, the truncated and intact enzymes had the same DNA polymerase specific activity with $(Cm)_n \cdot (dG)_{12-18}$. However, the truncated enzyme copied $(A)_n \cdot (dT)_{12-18}$ only one fourth as efficiently as the parent RT. The origin of this difference has not yet been established.

TABLE 1

DNA polymerase and RNase H activity in extracts of heat induced E. coli KB02 (lambda) bearing pRT601 or one of its derivatives.

| Plasmid | DNA poilymerase Activity[a] (cpm incorporated/2.5 μl extract) | RNase H Activity[b] (cpm solubilized/2.5 μl extract) |
|---|---|---|
| pRT601 | 10,977 | 2,020 |
| pRTdBam-Bam | 179 | 1,564 |
| pRTdEcoRV-C | 10,038 | 268 |

[a]Reverse transcriptase DNA polymerase activity was assayed with $(Cm)_n \cdot (dG)_{12-18}$ (materials and Methods).
[b]RNase H activity was assayed with $[^3H](A)_n \cdot (dT)_n$ (Materials and Methods).

TABLE 2

Comparison of activities of purified RT coded by pRT601, pRT603, and pRTdEcoRV-C

| | DNA Polymerase Activity with | | |
|---|---|---|---|
| Enzyme | $(Cm)_n \cdot (dG)_{12-18}$ (Units/mg) | $(A)_n \cdot (dT)_{12-18}$ (Units/mg) | RNase H Activity (Units/mg) |
| pRT601 | 21,700 | 350,000 | 2,670 |
| pRT603 | ND[a] | 230,000 | 1,100 |
| pRTdEcoRV-C | 17,500 | 81,000 | —[b] |

[a]ND, not determined
[b]No activity was detected

TABLE 3

Summary of the purification of pRTdEcoRV-C RT

| | | DNA Polymerase Activity[a] | | | RNase H Activity | | |
|---|---|---|---|---|---|---|---|
| Fraction | Total Protein[c] (mg) | Total (Units) × $10^3$ | Specific Activity (Units/mg) × $10^3$ | Yield (%) | Total (Units) × $10^3$ | Specific Activity (Units/mg) × $10^3$ | Yield (%) |
| Crude lysate | 7,913 | 255 | 0.03 | 100 | 80 | 0.01 | 100 |
| Polymin P Supernatant | 2,735 | 323 | 0.12 | 127 | 157 | 0.06 | 196 |
| $(NH_4)_2SO_4$ pellet | 63 | 168 | 1.38 | 66 | 6.0 | 0.10 | 7 |
| Phosphocellulose pool | 8.8 | 167 | 19.0 | 66 | 2.0 | 0.23 | 3 |
| Heparin-agarose pool | 6.5 | 111 | 17.1 | 44 | —[b] | — | — |
| Mono S pool | 3.1 | 55 | 17.5 | 22 | —[b] | — | — |

[a]DNA polymerase activity was assayed with $(Cm)_n \cdot (dG)_{12-18}$
[b]No activity could be detected
[c]Protein concentrations were determined using bovine serum albumin as standard according to Lowry, O. H., et al., J. Biol. Chem. 239:222–230 (1964).

What is claimed is:

1. An isolated polypeptide having DNA polymerase activity and substantially reduced RNase H activity, wherein said polypeptide is encoded by a modified reverse transcriptase nucleotide sequence that encodes a modified amino acid sequence resulting in said polypeptide having substantially reduced RNase H activity, and wherein said nucleotide sequence is derived from an organism selected from the group consisting of a retrovirus, yeast, Neurospora, Drosophila, primates and rodents.

2. The polypeptide of claim 1, wherein said nucleotide sequence is derived from an organism selected from the group consisting of M-MLV, HTLV-1, BLV, and HIV.

3. The polypeptide of claim 1, wherein said polypeptide has no detectable RNase H activity.

4. The polypeptide of claim 1, wherein said polypeptide lacks RNase H activity.

5. The polypeptide of claim 1, wherein said polypeptide may be used in the preparation of full length cDNA.

6. The polypeptide of claim 5, wherein said preparation of full length cDNA may be accomplished without significant degradation of an mRNA template.

7. The polypeptide of claim 1, wherein said polypeptide allows the preparation of cDNA without significant degradation of an mRNA template.

8. The polypeptide of claim 1, wherein said polypeptide allows preparation of cDNA without significant degradation of an mRNA template as determined by gel electrophoresis.

9. The polypeptide of claim 1, wherein said polypeptide does not significantly degrade an mRNA template during first strand DNA synthesis.

10. The polypeptide of claim 1, wherein said polypeptide does not significantly degrade an mRNA template during a cDNA synthesis reaction as shown in FIG. 5.

11. The polypeptide of claim 1, wherein said polypeptide does not significantly degrade an mRNA template during a one minute cDNA synthesis reaction as shown in FIG. 5.

12. The polypeptide of claim 1, wherein said polypeptide allows an mRNA template to remain intact during cDNA synthesis as shown in FIG. 5.

13. The polypeptide of claim 1, wherein said polypeptide allows an mRNA template to remain intact during a one minute cDNA synthesis reaction as shown in FIG. 5.

14. The polypeptide of claim 1, wherein said reduction of RNase H activity is determined by examining the integrity of an mRNA template during cDNA synthesis.

15. The polypeptide of claim 1, wherein said reduction of RNase H activity is determined by examining the integrity of an mRNA template by gel electrophoresis as shown in FIG. 5.

16. The polypeptide of claim 1, wherein said reduction of RNase H activity is determined by examining the integrity of an mRNA template during a one minute cDNA synthesis reaction as shown in FIG. 5.

17. The polypeptide of claim 1, wherein said polypeptide can synthesize cDNA from an mRNA template.

18. The polypeptide of claim 17, wherein said polypeptide can synthesize full length cDNA.

19. The polypeptide of claim 17, wherein said polypeptide can synthesize cDNA without significant degradation of said mRNA template.

20. The polypeptide of claim 1, wherein said nucleotide sequence is derived from a Moloney Murine Leukemia virus (M-MLV) nucleotide sequence.

21. The polypeptide of claim 1, wherein said nucleotide sequence is derived from a retrovirus nucleotide sequence.

22. An isolated polypeptide having DNA polymerase activity and reduced RNase H activity, wherein said polypeptide is encoded by a modified reverse transcriptase nucleotide sequence that encodes a modified amino acid sequence resulting in said polypeptide having reduced RNase H activity, and wherein said polypeptide does not significantly degrade an mRNA template during first strand cDNA synthesis as determined by gel electrophoresis, and wherein said nucleotide sequence is derived from an organism selected from the group consisting of a retrovirus, yeast, Neurospora, Drosophila, primates and rodents.

23. The polypeptide of claim 22, wherein said nucleotide sequence is an N-MLV nucleotide sequence.

24. The polypeptide of claim 22, wherein said polypeptide does not significantly degrade an mRNA template during cDNA synthesis as shown in FIG. 5.

25. The polypeptide of claim 22, wherein said polypeptide does not significantly degrade an mRNA template during a one minute cDNA synthesis reaction as shown in FIG. 5.

26. The polypeptide of claim 22, wherein said polypeptide does not significantly degrade an mRNA template during a five minute cDNA synthesis reaction as shown in FIG. 5.

27. The polypeptide of claim 22, wherein said polypeptide does not significantly degrade an mRNA template during a 10 minute cDNA synthesis reaction as shown in FIG. 5.

28. The polypeptide of claim 22, wherein said polypeptide does not significantly degrade an mRNA template during a 30 minute cDNA synthesis reaction as shown in FIG. 5.

29. The polypeptide of claim 22, wherein said polypeptide does not significantly degrade an mRNA template during a 60 minute cDNA synthesis reaction as shown in FIG. 5.

30. An isolated reverse transcriptase having DNA polymerase activity and substantially reduced RNase H activity, wherein said reverse transcriptase is encoded by a modified nucleotide sequence that encodes a modified amino acid sequence resulting in said reverse transcriptase having substantially reduced RNase H activity, and wherein said nucleotide sequence is derived from an organism selected from the group consisting of a retrovirus, yeast, Neurospora, Drosophila, primates and rodents.

31. The reverse transcriptase of claim 30, wherein said reverse transcriptase has no detectable RNase H activity.

32. The reverse transcriptase of claim 30, wherein said reverse transcriptase lacks RNase H activity.

33. The reverse transcriptase of claim 30, wherein said reverse transcriptase may be used in the preparation of full length cDNA.

34. The reverse transcriptase of claim 33, wherein said preparation of full length cDNA may be accomplished without significant degradation of an mRNA template.

35. The reverse transcriptase of claim 30, wherein said reverse transcriptase allows the preparation of cDNA without significant degradation of an mRNA template.

36. The reverse transcriptase of claim 30, wherein said reverse transcriptase allows preparation of cDNA without significant degradation of an mRNA template as determined by gel electrophoresis.

37. The reverse transcriptase of claim 32, wherein said reverse transcriptase does not significantly degrade an mRNA template during first strand DNA synthesis.

38. The reverse transcriptase of claim 30, wherein said reverse transcriptase does not significantly degrade an mRNA template during a cDNA synthesis reaction as shown in FIG. 5.

39. The reverse transcriptase of claim 30, wherein said reverse transcriptase does not significantly degrade an mRNA template during a one minute cDNA synthesis reaction as shown in FIG. 5.

40. The reverse transcriptase of claim 30, wherein said reverse transcriptase allows an mRNA template to remain intact during a cDNA synthesis reaction as shown in FIG. 5.

41. The reverse transcriptase of claim 30, wherein said reverse transcriptase allows an mRNA template to remain intact during a one minute cDNA synthesis reaction as shown in FIG. 5.

42. The reverse transcriptase of claim 30, wherein said reduction of RNase H activity is determined by examining the integrity of an mRNA template during cDNA synthesis.

43. The reverse transcriptase of claim 30, wherein said reduction of RNase H activity is determined by examining the integrity of an mRNA template during a cDNA synthesis reaction by gel electrophoresis as shown in FIG. 5.

44. The reverse transcriptase of claim 30, wherein said reduction of RNase H activity is determined by examining the integrity of an mRNA template during a one minute reaction as shown in FIG. 5.

45. The reverse transcriptase of claim 30, wherein said reverse transcriptase can synthesize cDNA from an mRNA template.

46. The reverse transcriptase of claim 45, wherein said reverse transcriptase can synthesize full length cDNA.

47. The reverse transcriptase of claim 45, wherein said reverse transcriptase can synthesize cDNA without significant degradation of said mRNA template.

48. The reverse transcriptase of claim 30, wherein said nucleotide sequence is derived from a Moloney Murine Leukemia virus (M-MLV) nucleotide sequence.

49. The reverse transcriptase of claim 30, wherein said nucleotide sequence is derived from a human T-cell leukemia type I (HTLV-1) nucleotide sequence.

50. The reverse transcriptase of claim 30, wherein said nucleotide sequence is derived from a bovine leukemia virus (BLV) nucleotide sequence.

51. The reverse transcriptase of claim 30, wherein said nucleotide sequence is derived from a Rous sarcoma virus (RSV) nucleotide sequence.

52. The reverse transcriptase of claim 30, wherein said nucleotide sequence is derived from a human immunodeficiency virus (HIV) nucleotide sequence.

53. The reverse transcriptase of claim 30, wherein said nucleotide sequence is derived from a retrovirus nucleotide sequence.

54. An isolated reverse transcriptase having DNA polymerase activity and reduced RNase H activity, wherein said reverse transcriptase is encoded by a modified nucleotide sequence that encodes a modified amino acid sequence resulting in said reverse transcriptase having reduced RNase H activity, and wherein said reverse transcriptase does not significantly degrade an mRNA template during first stand cDNA synthesis as determined by gel electrophoresis, and wherein said nucleotide sequence is derived from an organism selected from the group consisting of a retrovirus, yeast, Neurospora, Drosophila, primates and rodents.

55. The reverse transcriptase of claim 54, wherein said reverse transcriptase does not significantly degrade an mRNA template during a cDNA synthesis reaction as shown in FIG. 5.

56. The reverse transcriptase of claim 54, wherein said reverse transcriptase does not significantly degrade an mRNA template during a one minute cDNA synthesis reaction as shown in FIG. 5.

57. The reverse transcriptase of claim 54, wherein said reverse transcriptase does not significantly degrade an mRNA template during a five minute cDNA synthesis reaction as shown in FIG. 5.

58. The reverse transcriptase of claim 54, wherein said reverse transcriptase does not significantly degrade an mRNA template during a 10 minute cDNA synthesis reaction as shown in FIG. 5.

59. The reverse transcriptase of claim 54, wherein said reverse transcriptase does not significantly degrade an mRNA template during a 30 minute cDNA synthesis reaction as shown in FIG. 5.

60. The reverse transcriptase of claim 54, wherein said reverse transcriptase does not significantly degrade an mRNA template during a 60 minute cDNA synthesis reaction as shown in FIG. 5.

61. The polypeptide of claim 54, wherein said nucleotide sequence is an N-MLV nucleotide sequence.

62. An isolated reverse transcriptase having DNA polymerase activity and substantially reduced RNase H activity, which is obtained by a process comprising
   (a) modifying a nucleotide sequence coding for a reverse transcriptase to provide a modified nucleotide sequence that codes for said reverse transcriptase, wherein said nucleotide sequence is derived from an organism selected from the group consisting of a retrovirus, yeast, Neurospora, Drosophila, primates and rodents;

(b) transforming a host cell with said modified nucleotide sequence;

(c) culturing the transformed host cell under conditions which produce said reverse transcriptase; and (d) isolating said reverse transcriptase.

63. The reverse transcriptase of claim 62, wherein said reverse transcriptase has no detectable RNase H activity.

64. The reverse transcriptase of claim 62, wherein said reverse transcriptase lacks RNase H activity.

65. The reverse transcriptase of claim 62, wherein said reverse transcriptase may be used in the preparation of full length cDNA.

66. The reverse transcriptase of claim 65, wherein said preparation of full length cDNA may be accomplished without significant degradation of an mRNA template.

67. The reverse transcriptase of claim 62, herein said reverse transcriptase allows the preparation of cDNA without significant degradation of an mRNA template.

68. The reverse transcriptase of claim 62, wherein said reverse transcriptase allows preparation of cDNA without significant degradation of an mRNA template as determined by gel electrophoresis.

69. The reverse transcriptase of claim 62, wherein said reverse transcriptase does not significantly degrade an mRNA template during first strand DNA synthesis.

70. The reverse transcriptase of claim 62, wherein said reverse transcriptase does not significantly degrade an mRNA template during cDNA synthesis as shown in FIG. 5.

71. The reverse transcriptase of claim 62, wherein said reverse transcriptase does not significantly degrade an mRNA template during a one minute cDNA synthesis reaction as shown in FIG. 5.

72. The reverse transcriptase of claim 62, wherein said reverse transcriptase allows an mRNA template to remain intact during a cDNA synthesis reaction as shown in FIG. 5.

73. The reverse transcriptase of claim 62, wherein said reverse transcriptase allows an mRNA template to remain intact during a one minute cDNA synthesis reaction as shown in FIG. 5.

74. The reverse transcriptase of claim 62, wherein said reduction of RNase H activity is determined by examining the integrity of an mRNA template during cDNA synthesis.

75. The reverse transcriptase of claim 62, wherein said reduction of RNase H activity is determined by examining the integrity of an mRNA template by gel electrophoresis as shown in FIG. 5.

76. The reverse transcriptase of claim 62, wherein said reduction of RNase H activity is determined by examining the integrity of an mRNA template during a one minute cDNA synthesis reaction as shown in FIG. 5.

77. The reverse transcriptase of claim 62, wherein said reverse transcriptase can synthesize cDNA from an mRNA template.

78. The reverse transcriptase of claim 77, wherein said reverse transcriptase can synthesize full length cDNA.

79. The reverse transcriptase of claim 77, wherein said reverse transcriptase can synthesize cDNA without significant degradation of said mRNA template.

80. The reverse transcriptase of claim 62, wherein said reverse transcriptase is a Moloney Murine Leukemia virus (M-MLV) reverse transcriptase.

81. The reverse transcriptase of claim 62, wherein said reverse transcriptase is a human T-cell leukemia type I (HTLV-1) reverse transcriptase.

82. The reverse transcriptase of claim 62, wherein said reverse transcriptase is a bovine leukemia virus (BLV) reverse transcriptase.

83. The reverse transcriptase of claim 62, wherein said reverse transcriptase is a Rous sarcoma virus (RSV) reverse transcriptase.

84. The reverse transcriptase of claim 62, wherein said reverse transcriptase is a human immunodeficiency virus (HIV) reverse transcriptase.

85. The reverse transcriptase of claim 62, wherein said reverse transcriptase is a retrovirus reverse transcriptase.

86. An isolated reverse transcriptase having DNA polymerase activity and reduced RNase H activity, which is obtained by a process comprising (a) modifying a nucleotide sequence coding for a reverse transcriptase to provide a modified nucleotide sequence that codes for said reverse transcriptase, wherein said nucleotide sequence is derived from an organism selected from the group consisting of a retrovirus, yeast, Neurospora, Drosophila, primates and rodents;

(b) transforming a host cell with said modified nucleotide sequence;

(c) culturing the transformed host cell under conditions which produce said reverse transcriptase; and (d) isolating said reverse transcriptase;

wherein said reverse transcriptase does not significantly degrade an mRNA template during first strand cDNA synthesis as determined by gel electrophoresis.

87. The reverse transcriptase of claim 86, wherein said reverse transcriptase does not significantly degrade an mRNA template during a cDNA synthesis reaction as shown in FIG. 5.

88. The reverse transcriptase of claim 86, wherein said reverse transcriptase does not significantly degrade an mRNA template during a one minute cDNA synthesis reaction as shown in FIG. 5.

89. The reverse transcriptase of 86, wherein said reverse transcriptase does not significantly degrade an mRNA template during a five minute cDNA synthesis reaction as shown in FIG. 5.

90. The reverse transcriptase of claim 86, wherein said reverse transcriptase does not significantly degrade an mRNA template during a 10 minute cDNA synthesis reaction as shown in FIG. 5.

91. The reverse transcriptase of claim 86, wherein said reverse transcriptase does not significantly degrade an mRNA template during a 30 minute cDNA synthesis reaction as shown in FIG. 5.

92. The reverse transcriptase of claim 86, wherein said reverse transcriptase does not significantly degrade an mRNA template during a 60 minute cDNA synthesis reaction as shown in FIG. 5.

93. The polypeptide of claim 86, wherein said nucleotide sequence is an M-MLV nucleotide sequence.

94. An isolated recombinantly produced reverse transcriptase having DNA polymerase activity and substantially reduced RNase H activity, wherein said reverse transcriptase is encoded by a nucleotide sequence derived from an organism selected from the group consisting of a retrovirus, yeast, Neurospora, Drosophila, primates and rodents.

95. The reverse transcriptase of claim 94, wherein said reverse transcriptase has no detectable RNase H activity.

96. The reverse transcriptase of claim 94, wherein said reverse transcriptase lacks RNase H activity.

97. The reverse transcriptase of claim 94, wherein said reverse transcriptase may be used in the preparation of full length cDNA.

98. The reverse transcriptase of claim 97, wherein said preparation of full length cDNA may be accomplished without significant degradation of an mRNA template.

99. The reverse transcriptase of claim 94, wherein said reverse transcriptase allows the preparation of cDNA without significant degradation of an mRNA template.

100. The reverse transcriptase of claim 94, wherein said reverse transcriptase does not significantly degrade an mRNA template during a cDNA synthesis reaction as shown in FIG. 5.

101. The reverse transcriptase of claim 94, wherein said reverse transcriptase does not significantly degrade an mRNA template during a one minute cDNA synthesis reaction as shown in FIG. 5.

102. The reverse transcriptase of claim 94, wherein said reverse transcriptase allows an mRNA template to remain intact during a cDNA synthesis reaction as shown in FIG. 5.

103. The reverse transcriptase of claim 94, wherein said reverse transcriptase allows an mRNA template to remain intact during a one minute cDNA synthesis reaction as shown in FIG. 5.

104. The reverse transcriptase of claim 94, wherein said reduction of RNase H activity is determined by examining the integrity of an mRNA template during a cDNA synthesis reaction.

105. The reverse transcriptase of claim 94, wherein said reduction of RNase H activity is determined by examining the integrity of an mRNA template by gel electrophoresis as shown in FIG. 5.

106. The reverse transcriptase of claim 94, wherein said reduction of RNase H activity is determined by examining the integrity of an mRNA template during a one minute cDNA synthesis reaction as shown in FIG. 5.

107. The reverse transcriptase of claim 94, wherein said reverse transcriptase can synthesize cDNA from an mRNA template.

108. The reverse transcriptase of claim 107, wherein said reverse transcriptase can synthesize full length cDNA.

109. The reverse transcriptase of claim 107, wherein said reverse transcriptase can synthesize cDNA without significant degradation of said mRNA template.

110. The reverse transcriptase of claim 94, wherein said reverse transcriptase is a Moloney Murine Leukemia virus (M-MLV) reverse transcriptase.

111. The reverse transcriptase of claim 94, wherein said reverse transcriptase is a human T-cell leukemia type I (HTLV-1) reverse transcriptase.

112. The reverse transcriptase of claim 94, wherein said reverse transcriptase is a bovine leukemia virus (BLV) reverse transcriptase.

113. The reverse transcriptase of claim 94, wherein said reverse transcriptase is a Rous sarcoma virus (RSV) reverse transcriptase.

114. The reverse transcriptase of claim 94, wherein said reverse transcriptase is a human immunodeficiency virus (HIV) reverse transcriptase.

115. The reverse transcriptase of claim 94, wherein said reverse transcriptase is a retrovirus reverse transcriptase.

116. An isolated recombinantly produced reverse transcriptase having DNA polymerase activity and reduced RNase H activity, wherein said reverse transcriptase allows preparation of cDNA without significant degradation of an mRNA template as determined by gel electrophoresis, and wherein said reverse transcriptase is encoded by a nucleotide sequence derived from an organism selected from the group consisting of a retrovirus, yeast, Neurospora, Drosophila, primates and rodents.

117. The reverse transcriptase of claim 116, wherein said reverse transcriptase does not significantly degrade an mRNA template during first strand DNA synthesis.

118. The reverse transcriptase of claim 116, wherein said reverse transcriptase does not significantly degrade an mRNA template during first strand DNA synthesis as determined by gel electrophoresis.

119. The reverse transcriptase of claim 116, wherein said reverse transcriptase does not significantly degrade an mRNA template during a cDNA synthesis reaction as shown in FIG. 5.

120. The reverse transcriptase of claim 116, wherein said reverse transcriptase does not significantly degrade an mRNA template during a one minute cDNA synthesis reaction as shown in FIG. 5.

121. The reverse transcriptase of claim 116, wherein said reverse transcriptase does not significantly degrade an mRNA template during a five minute cDNA synthesis reaction as shown in FIG. 5.

122. The reverse transcriptase of claim 116, wherein said reverse transcriptase does not significantly degrade an mRNA template during a 10 minute cDNA synthesis reaction as shown in FIG. 5.

123. The reverse transcriptase of claim 116, wherein said reverse transcriptase does not significantly degrade an mRNA template during a 30 minute cDNA synthesis reaction as shown in FIG. 5.

124. The reverse transcriptase of claim 116, wherein said reverse transcriptase does not significantly degrade an mRNA template during a 60 minute cDNA synthesis reaction as shown in FIG. 5.

125. The polypeptide of claim 116, wherein said recombinantly produced reverse transcriptase is encoded by an M-MLV nucleotide sequence.

126. An isolated polypeptide having DNA polymerase activity and reduced RNase H activity, wherein said polypeptide is encoded by a modified reverse transcriptase nucleotide sequence that encodes an amino acid sequence modified in the region corresponding to amino acids 498–611 of M-MLV reverse transcriptase so that the encoded polypeptide has reduced RNase H activity, and wherein said polypeptide is encoded by a nucleotide sequence derived from an organism selected from the group consisting of a retrovirus, yeast, Neurospora, Drosophila, primates and rodents.

127. The polypeptide of claim 126, wherein said reverse transcriptase nucleotide sequence is selected from the group consisting of M-MLV, HTLV-1, BLV, and HIV reverse transcriptase nucleotide sequences.

128. The polypeptide of claim 126, wherein said nucleotide sequence is derived from a retrovirus nucleotide sequence.

129. The polypeptide of claim 126, wherein said region corresponds to amino acids 503–611 of the M-MLV reverse transcriptase.

130. The polypeptide of claim 126, wherein said reverse transcriptase nucleotide sequence is a M-MLV nucleotide sequence.

131. The polypeptide of claim 126, wherein said polypeptide allows preparation of cDNA without significant degradation of an mRNA template as determined by gel electrophoresis.

132. The polypeptide of claim 126, wherein said polypeptide does not significantly degrade an mRNA template during first strand cDNA synthesis.

133. The polypeptide of claim 126, wherein said polypeptide does not significantly degrade an mRNA template during cDNA synthesis as shown in FIG. 5.

134. The polypeptide of claim 126, wherein said polypeptide does not significantly degrade an mRNA template during a one minute cDNA synthesis reaction as shown in FIG. 5.

135. The polypeptide of claim 126, wherein said polypeptide does not significantly degrade an mRNA template during a five minute cDNA synthesis reaction as shown in FIG. 5.

136. The polypeptide of claim 126, wherein said polypeptide does not significantly degrade an mRNA template during a 10 minute cDNA synthesis reaction as shown in FIG. 5.

137. The polypeptide of claim 126, wherein said polypeptide does not significantly degrade an mRNA template during a 30 minute cDNA synthesis reaction as shown in FIG. 5.

138. The polypeptide of claim 126, wherein said polypeptide does not significantly degrade an mRNA template during a 60 minute cDNA synthesis reaction as shown in FIG. 5.

139. An isolated polypeptide having DNA polymerase activity and reduced RNase H activity, wherein said polypeptide is encoded by a reverse transcriptase nucleotide sequence that has been modified so that the encoded polypeptide has reduced RNase H activity, wherein said polypeptide is encoded by a nucleotide sequence derived from an organism selected from the group consisting of a retrovirus, yeast, Neurospora, Drosophila, primates and rodents, and wherein said polypeptide may be used for the preparation of cDNA of which at least 34% is full length.

140. The polypeptide of claim 139, wherein said nucleotide sequence is derived from an organism selected from the group consisting of M-MLV, HTLV-1, BLV, and HIV.

141. The polypeptide of claim 139, wherein said nucleotide sequence is derived from a retrovirus nucleotide sequence.

142. The polypeptide of claim 139, wherein said reverse transcriptase nucleotide sequence is a M-MLV nucleotide sequence.

143. The polypeptide of claim 139, wherein said polypeptide allows preparation of cDNA without significant degradation of an mRNA template as determined by gel electrophoresis.

144. The polypeptide of claim 139, wherein said polypeptide does not significantly degrade an mRNA template during first strand cDNA synthesis.

145. The polypeptide of claim 139, wherein said polypeptide does not significantly degrade an mRNA template during cDNA synthesis as shown in FIG. 5.

146. The polypeptide of claim 139, wherein said polypeptide does not significantly degrade an mRNA template during a one minute cDNA synthesis reaction as shown in FIG. 5.

147. The polypeptide of claim 139, wherein said polypeptide does not significantly degrade an mRNA template during a five minute cDNA synthesis reaction as shown in FIG. 5.

148. The polypeptide of claim 139, wherein said polypeptide does not significantly degrade an mRNA template during a 10 minute cDNA synthesis reaction as shown in FIG. 5.

149. The polypeptide of claim 139, wherein said polypeptide does not significantly degrade an mRNA template during a 30 minute cDNA synthesis reaction as shown in FIG. 5.

150. The polypeptide of claim 139, wherein said polypeptide does not significantly degrade an mRNA template during a 60 minute cDNA synthesis reaction as shown in FIG. 5.

151. An isolated polypeptide having DNA polymerase activity and reduced RNase H activity, wherein said polypeptide is encoded by a reverse transcriptase nucleotide sequence that has been modified so that the encoded polypeptide has reduced RNase H activity, wherein said nucleotide sequence is derived from an organism selected from the group consisting of a retrovirus, yeast, Neurospora, Drosophila, primates and rodents, wherein said polypeptide may be used for the preparation of full length cDNA, and wherein the amount of full length cDNA is at least 42% greater than the amount of full length cDNA obtained by a polypeptide encoded by said nucleotide sequence that has not been so modified.

152. The polypeptide of claim 151, wherein said nucleotide sequence is derived from an organism selected from the group consisting of M-MLV, HTLV-1, BLV, and HIV.

153. The polypeptide of claim 151, wherein said nucleotide sequence is derived from a retrovirus nucleotide sequence.

154. The polypeptide of claim 151, wherein said reverse transcriptase nucleotide sequence is a M-MLV nucleotide sequence.

155. The polypeptide of claim 151, wherein said polypeptide allows preparation of cDNA without significant degradation of an mRNA template as determined by gel electrophoresis.

156. The polypeptide of claim 151, wherein said polypeptide does not significantly degrade an mRNA template during first strand cDNA synthesis.

157. The polypeptide of claim 151, wherein said polypeptide does not significantly degrade an mRNA template during cDNA synthesis as shown in FIG. 5.

158. The polypeptide of claim 151, wherein said polypeptide does not significantly degrade an mRNA template during a one minute cDNA synthesis reaction as shown in FIG. 5.

159. The polypeptide of claim 151, wherein said polypeptide does not significantly degrade an mRNA template during a five minute cDNA synthesis reaction as shown in FIG. 5.

160. The polypeptide of claim 151, wherein said polypeptide does not significantly degrade an mRNA template during a 10 minute cDNA synthesis reaction as shown in FIG. 5.

161. The polypeptide of claim 151, wherein said polypeptide does not significantly degrade an mRNA template during a 30 minute cDNA synthesis reaction as shown in FIG. 5.

162. The polypeptide of claim 151, wherein said polypeptide does not significantly degrade an mRNA template during a 60 minute cDNA synthesis reaction as shown in FIG. 5.

163. An isolated polypeptide having DNA polymerase activity and substantially reduced RNase H activity, wherein said polypeptide is encoded by a modified reverse transcriptase nucleotide sequence that encodes an amino acid sequence modified within the RNase H domain so that the encoded polypeptide has substantially reduced RNase H activity.

164. The polypeptide of claim 163, wherein said nucleotide sequence is derived from an organism selected from the group consisting of a retrovirus, yeast, Neurospora, Drosophila, primates and rodents.

165. An isolated polypeptide having DNA polymerase activity and reduced RNase H activity, wherein said polypeptide is encoded by a modified reverse transcriptase nucleotide sequence that encodes an amino acid sequence modified within the RNase H domain so that the encoded polypeptide has reduced RNase H activity, and wherein said polypeptide does not significantly degrade an mRNA template during first strand cDNA synthesis as determined by gel electrophoresis.

166. The polypeptide of claim 165, wherein said nucleotide sequence is derived from an organism selected from the group consisting of a retrovirus, yeast, Neurospora, Drosophila, primates and rodents.

167. An isolated reverse transcriptase having DNA polymerase activity and substantially reduced RNase H activity, wherein said reverse transcriptase is encoded by a modified nucleotide sequence that encodes an amino acid sequence modified within the RNase H domain so that the encoded reverse transcriptase has substantially reduced RNase H activity.

168. The reverse transcriptase of claim 167, wherein said nucleotide sequence is derived from an organism selected from the group consisting of a retrovirus, yeast, Neurospora, Drosophila, primates and rodents.

169. An isolated reverse transcriptase having DNA polymerase activity and reduced RNase H activity, wherein said reverse transcriptase is encoded by a modified nucleotide sequence that encodes an amino acid sequence modified within the RNase H domain so that the encoded reverse transcriptase has reduced RNase H activity, and wherein said reverse transcriptase does not significantly degrade an mRNA template during first stand cDNA synthesis as determined by gel electrophoresis.

170. The reverse transcriptase of claim 169, wherein said nucleotide sequence is derived from an organism selected from the group consisting of a retrovirus, yeast, Neurospora, Drosophila, primates and rodents.

171. An isolated reverse transcriptase having DNA polymerase activity and substantially reduced RNase H activity, which is obtained by a process comprising
    (a) modifying within the RNase H domain of a nucleotide sequence coding for a reverse transcriptase to provide a modified nucleotide sequence that codes for said reverse transcriptase;
    (b) transforming a host cell with said modified nucleotide sequence;
    (c) culturing the transformed host cell under conditions which produce said reverse transcriptase; and
    (d) isolating said reverse transcriptase.

172. The reverse transcriptase of claim 171, wherein said nucleotide sequence is derived from an organism selected from the group consisting of a retrovirus, yeast, Neurospora, Drosophila, primates and rodents.

173. An isolated reverse transcriptase having DNA polymerase activity and reduced RNase H activity, which is obtained by a process comprising
    (a) modifying within the RNase H domain of a nucleotide sequence coding for a reverse transcriptase to provide a modified nucleotide sequence that codes for said reverse transcriptase;
    (b) transforming a host cell with said modified nucleotide sequence;
    (c) culturing the transformed host cell under conditions which produce said reverse transcriptase; and
    (d) isolating said reverse transcriptase;
wherein said reverse transcriptase does not significantly degrade am mRNA template during first strand cDNA synthesis as determined by gel electrophoresis.

174. The reverse transcriptase of claim 173, wherein said nucleotide sequence is derived from an organism selected from the group consisting of a retrovirus, yeast, Neurospora, Drosophila, primates and rodents.

175. An isolated recombinantly produced reverse transcriptase having DNA polymerase activity and substantially reduced RNase H activity, wherein said reverse transcriptase has been modified within the RNase H domain to give substantially reduced RNase H activity.

176. The reverse transcriptase of claim 175, wherein said reverse transcriptase is encoded by a nucleotide sequence derived from an organism selected from the group consisting of a retrovirus, yeast, Neurospora, Drosophila, primates and rodents.

177. An isolated recombinantly produced reverse transcriptase having DNA polymerase activity and reduced RNase H activity, wherein said reverse transcriptase has been modified within the RNase H domain to give substantially reduced RNase H activity, and wherein said reverse transcriptase allows preparation of cDNA without significant degradation of an mRNA template as determined by gel electrophoresis.

178. The reverse transcriptase of claim 177, wherein said reverse transcriptase is encoded by a nucleotide sequence derived from an organism selected from the group consisting of a retrovirus, yeast, Neurospora, Drosophila, primates and rodents.

179. An isolated polypeptide having DNA polymerase activity and reduced RNase H activity, wherein said polypeptide is encoded by a reverse transcriptase nucleotide sequence that has been modified within the RNase H domain so that the encoded polypeptide has reduced RNase H activity, and wherein said polypeptide may be used for the preparation of cDNA of which at least 34% is full length.

180. The polypeptide of claim 179, wherein said polypeptide is encoded by a nucleotide sequence derived from an organism selected from the group consisting of a retrovirus, yeast, Neurospora, Drosophila, primates and rodents.

181. An isolated polypeptide having DNA polymerase activity and reduced RNase H activity, wherein said polypeptide is encoded by a reverse transcriptase nucleotide sequence that has been modified within the RNase H domain so that the encoded polypeptide has reduced RNase H activity, wherein said polypeptide may be used for the preparation of full length cDNA, and wherein the amount of full length cDNA is at least 42% greater than the amount of full length cDNA obtained by a polypeptide encoded by said nucleotide sequence that has not been so modified.

182. The polypeptide of claim 181, wherein said nucleotide sequence is derived from an organism selected from the group consisting of a retrovirus, yeast, Neurospora, Drosophila, primates and rodents.

183. An isolated polypeptide having DNA polymerase activity and reduced RNase H activity, wherein said polypeptide is encoded by a modified reverse transcriptase nucleotide sequence that encodes an amino acid sequence modified within the RNase H domain corresponding to amino acids 498–611 of M-MLV reverse transcriptase so that the encoded polypeptide has reduced RNase H activity.

184. The polypeptide of claim 183, wherein said nucleotide sequence is derived from an organism selected from the group consisting of a retrovirus, yeast, Neurospora, Drosophila, primates and rodents.

185. An isolated DNA molecule comprising a nucleotide sequence encoding the polypeptide or reverse transcriptase of any one of claims 1, 22, 25, 30, 54, 56, 62, 86, 94, 116, 120, 126–134, 139, 151, 163, 165, 167, 169, 171, 173, 175, 177, 179, 181 and 183.

186. A vector comprising the DNA molecule of claim 185.

187. A host cell comprising the DNA molecule of claim 189.

188. A host cell comprising the vector of claim 155.

189. A method for preparing a DNA molecule, said method comprising:

mixing an mRNA template with the polypeptide or reverse transcriptase of any one of claims 1, 22, 25, 30, 54, 56, 62, 86, 94, 116, 120, 126–134, 139, 151, 163, 165, 167, 169, 171, 173, 175, 177, 179, 181 and 183; and incubating said mixture under conditions sufficient to make a first DNA molecule complementary to said mRNA template.

190. A method for producing a polypeptide or reverse transcriptase having DNA polymerase activity and reduced RNase H activity, said method comprising:

culturing the host cell of claim 187 under conditions sufficient to produce said polypeptide or reverse transcriptase; and isolating said polypeptide or reverse transcriptase.

191. A method for producing a polypeptide or reverse transcriptase having DNA polymerase activity and reduced RNase H activity, said method comprising:

culturing the host cell of claim 188 under conditions sufficient to produce said polypeptide or reverse transcriptase; and isolating said polypeptide or reverse transcriptase.

192. The method of claim 189, wherein said first DNA molecule is full length cDNA.

193. The method of claim 189, further comprising incubating said first DNA molecule under conditions sufficient to make a second DNA molecule complementary to said first DNA molecule.

194. The method of claim 193, wherein said first and second DNA molecule form a double stranded DNA molecule.

195. A kit for the preparation of cDNA, said kit comprising a container containing the polypeptide or reverse transcriptase of any one of claims 1, 22, 25, 30, 54, 56, 62, 86, 94, 116, 120, 126–134, 139, 151, 163, 165, 167, 169, 171, 173, 175, 177, 179, 181, and 183.

196. The kit of claim 195, said kit further comprising one or more additional containers selected from the group consisting of:

a container containing one or more nucleoside triphosphates;

a container containing an oligo (dT) primer; and a container containing a buffer suitable for use in making cDNA.

* * * * *

UNITED STATES PATENT AND TRADEMARK OFFICE
CERTIFICATE OF CORRECTION

PATENT NO. : 6,063,608

DATED : May 16, 2000

INVENTORS : Kotewicz *et al.*

It is certified that an error appears in the above-identified patent and that said Letters Patent is hereby corrected as shown below.

In column 21, line 36, claim 37, please delete "32" and insert therefor --30--.

In column 22, claim 61, line 60, please delete "N-MLV" and insert therefor --M-MLV--.

At column 23, line 18, claim 67, please delete "herein" and insert therefor --wherein--.

At column 29, line claim 173, line 62, please delete "am" and insert therefor --an--.

Signed and Sealed this

First Day of May, 2001

Attest:

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT NO. : 6,063,608
DATED : May 16, 2000
INVENTOR(S) : Kotewicz et al.

It is certified that error appears in the above-identified patent and that said Letters Patent is hereby corrected as shown below:

Column 30, claim 187,
Line 67, please delete "189" and insert therein -- 185 -- .

Column 31, claim 188,
Line 1, please delete "155" and insert therein -- 186 -- .

Signed and Sealed this

Twentieth Day of November, 2001

*Attest:*

NICHOLAS P. GODICI
*Attesting Officer*     *Acting Director of the United States Patent and Trademark Office*